(12) United States Patent
Fukuda et al.

(10) Patent No.: US 7,740,621 B2
(45) Date of Patent: *Jun. 22, 2010

(54) MEDICAL NEEDLE AND MEDICAL DEVICE

(75) Inventors: Mitsuo Fukuda, Hyogo (JP); Seiji Aoyagi, Osaka (JP)

(73) Assignee: Lightnix, Inc., Hyogo (JP)

( * ) Notice: Subject to any disclaimer, the term of this patent is extended or adjusted under 35 U.S.C. 154(b) by 1154 days.

This patent is subject to a terminal disclaimer.

(21) Appl. No.: 10/524,487

(22) PCT Filed: Dec. 16, 2004

(86) PCT No.: PCT/JP2004/018781

§ 371 (c)(1),
(2), (4) Date: Oct. 28, 2005

(87) PCT Pub. No.: WO2005/058162

PCT Pub. Date: Jun. 30, 2005

(65) Prior Publication Data

US 2006/0100654 A1  May 11, 2006

(30) Foreign Application Priority Data

Dec. 19, 2003 (JP) .............................. 2003-422999

(51) Int. Cl.
*A61M 5/32* (2006.01)
(52) U.S. Cl. ..................................................... 604/273
(58) Field of Classification Search ................. 604/160, 604/271–274, 21, 239, 117, 118, 46, 506
See application file for complete search history.

(56) References Cited

U.S. PATENT DOCUMENTS 3,492,992 A  2/1970  Kurtz (Continued)

FOREIGN PATENT DOCUMENTS

EP  0 137 975 B1  4/1985

(Continued)

OTHER PUBLICATIONS

European Search Report (dated Feb. 22, 2008) for counterpart European Patent Application No. 04807140.1-2319 is provided for the purposes of certification under 37 C.F.R. §§ 1.97(e) and 1.704(d).

(Continued)

*Primary Examiner*—Nicholas D Lucchesi
*Assistant Examiner*—Diva Ranade
(74) *Attorney, Agent, or Firm*—Harness, Dickey & Pierce, P.L.C.

(57) ABSTRACT

One of the aspects of the present invention is to provide a medical needle extending along a predetermined direction and having a vertical cross-section taken along a plane perpendicular to the predetermined direction of which cross-sectional area varies based upon a distance from a needle tip. The medical needle includes a plurality of maximal points where the cross-sectional area of the vertical cross-section is locally maximal, and a plurality of minimal points where the cross-sectional area of the vertical cross-section is locally minimal. The vertical cross-section at the maximal point closest to the needle tip has the cross-sectional area not less than those at any other maximal points.

20 Claims, 29 Drawing Sheets

U.S. PATENT DOCUMENTS

| | | | | |
|---|---|---|---|---|
| 4,924,865 | A * | 5/1990 | Bays et al. | 606/77 |
| 5,250,066 | A | 10/1993 | Lambert | |
| 5,752,942 | A | 5/1998 | Doyle et al. | |
| 5,766,163 | A * | 6/1998 | Mueller et al. | 606/7 |
| 6,183,444 | B1 * | 2/2001 | Glines et al. | 604/187 |
| 6,290,702 | B1 * | 9/2001 | Fucci et al. | 606/323 |
| 6,551,343 | B1 * | 4/2003 | Tormala et al. | 606/213 |
| 6,623,492 | B1 * | 9/2003 | Berube et al. | 606/151 |
| 6,673,058 | B2 * | 1/2004 | Snow | 604/506 |
| 6,692,499 | B2 * | 2/2004 | Tormala et al. | 606/213 |
| 6,902,547 | B2 * | 6/2005 | Aves et al. | 604/272 |
| 7,211,088 | B2 * | 5/2007 | Grafton et al. | 606/77 |
| 7,361,182 | B2 * | 4/2008 | Fukuda et al. | 606/181 |
| 7,445,616 | B2 * | 11/2008 | Petrakis | 604/890.1 |
| 2002/0082543 | A1 | 6/2002 | Park et al. | |
| 2003/0028125 | A1 | 2/2003 | Yuzhakov et al. | |
| 2004/0131437 | A1 | 7/2004 | Kasai et al. | |
| 2004/0249394 | A1 * | 12/2004 | Morris et al. | 606/144 |
| 2005/0215977 | A1 * | 9/2005 | Uschold | 604/506 |
| 2006/0259006 | A1 * | 11/2006 | McKay et al. | 604/506 |

FOREIGN PATENT DOCUMENTS

| | | |
|---|---|---|
| EP | 1 346 686 | 9/2003 |
| JP | UM 53-68594 (A) | 6/1978 |
| JP | 61-31167 (A) | 2/1986 |
| JP | 4220334 A | 8/1992 |
| JP | 2001-509399 | 7/2001 |
| JP | 2002-45423 (A) | 2/2002 |
| JP | 2003-116821 A | 4/2003 |
| JP | 2003116962 | 4/2003 |
| JP | 2003-275327 A | 9/2003 |
| WO | WO 99/00155 | 1/1999 |
| WO | WO 03/037403 | 5/2003 |
| WO | WO 03/059431 A1 | 7/2003 |

OTHER PUBLICATIONS

PCT International Search Report issued on Feb. 1, 2005.
Oka et al., "Fabrication of a Micro Needle for a Trace Blood Test," Mar. 7, 2001 (pp. 59-62).
Kazunari Oka et al., "Fabrication of a Micro Needle for a Trace Blood Test," Fifth Kansai University Advanced Technology Symposium, Mar. 7, 2001, pp. 59-62 (partial English translation).
Office Action for European patent application No. 04807140.1 dated Jun. 22, 2009.
Japanese Office Action No. 2006-199495 dated Nov. 10, 2009.
European Search Report for Application No. 04 807 140.1 —2319 dated Nov. 9, 2009.

* cited by examiner

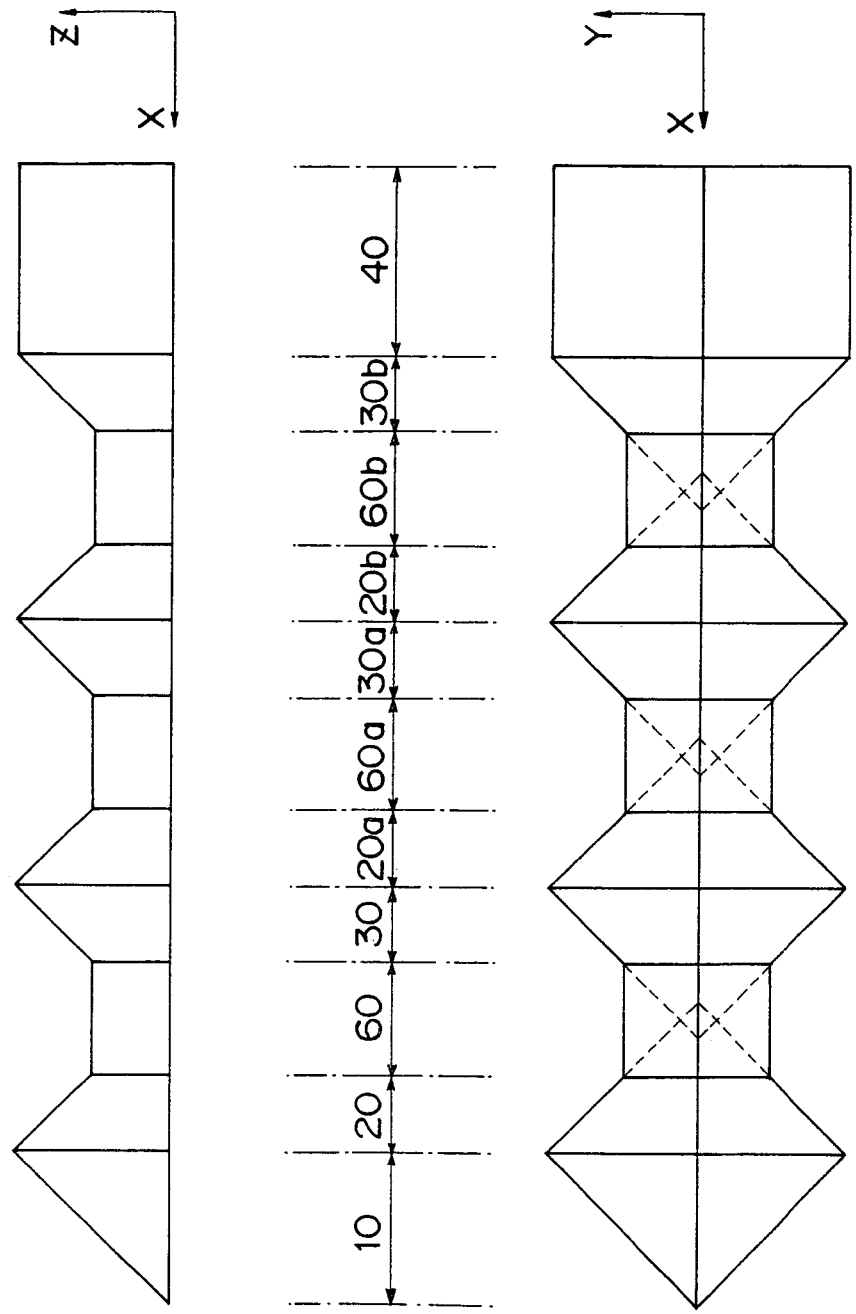

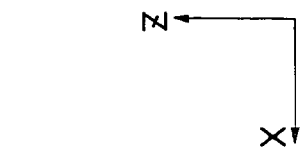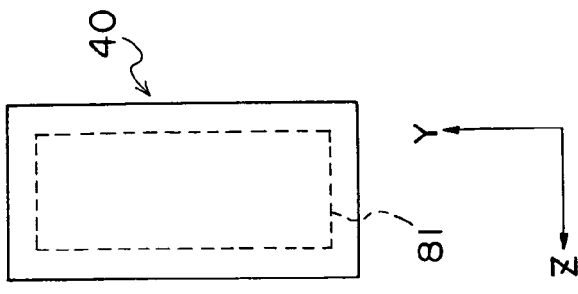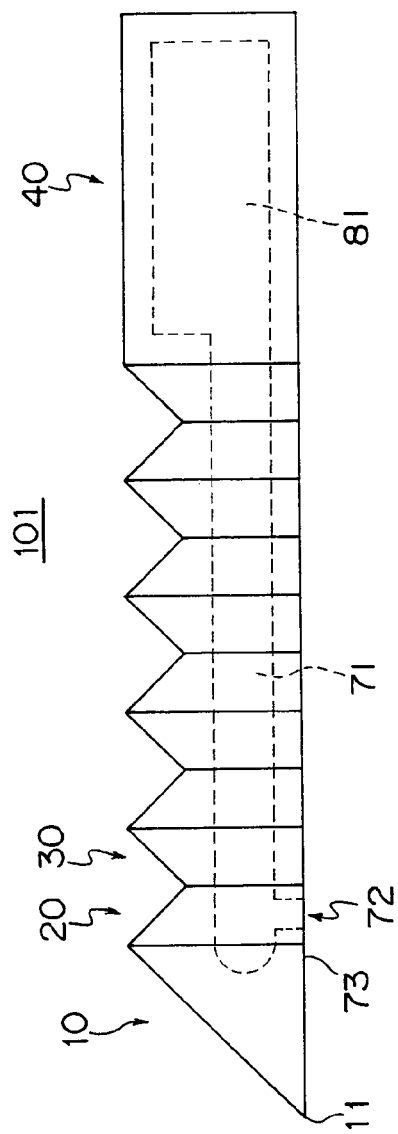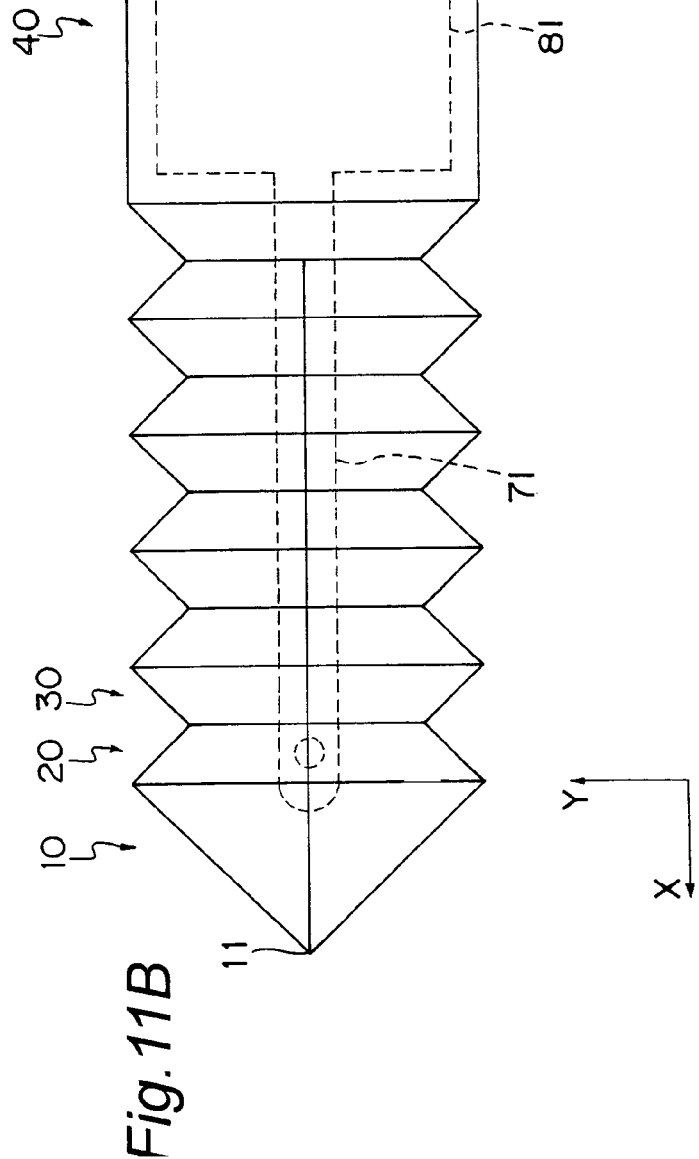

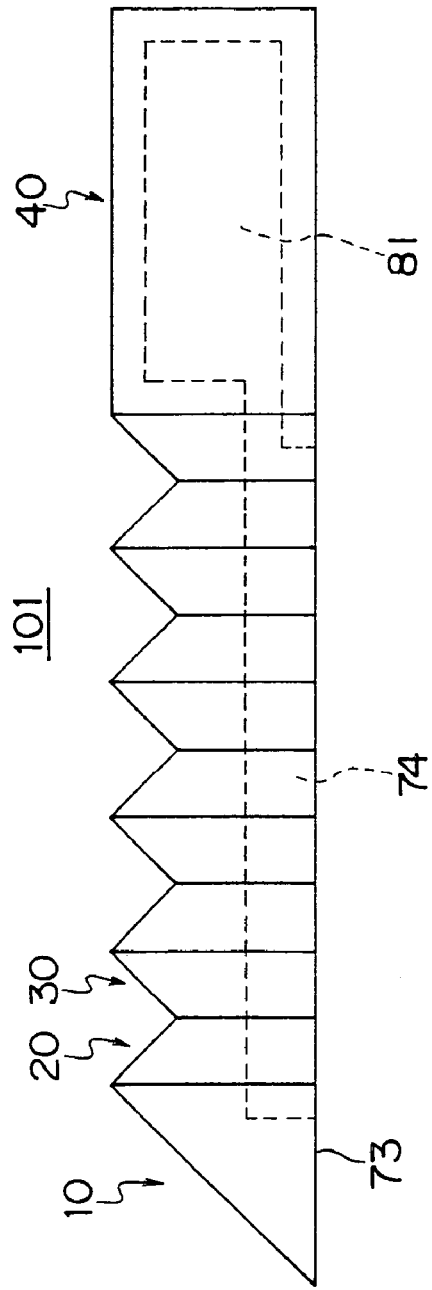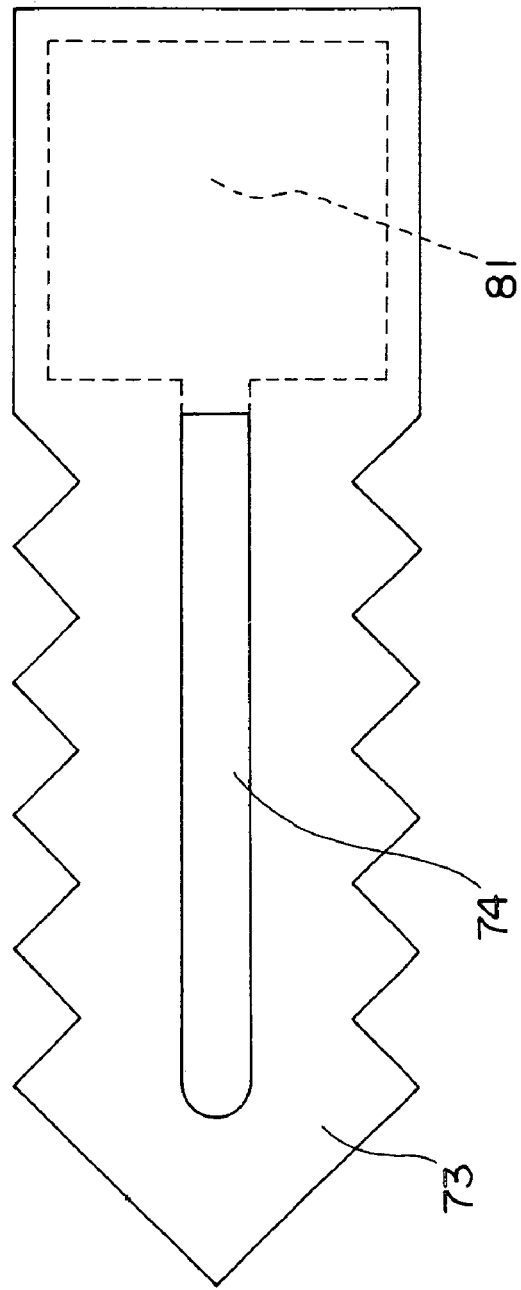
Fig. 12A
Fig. 12B

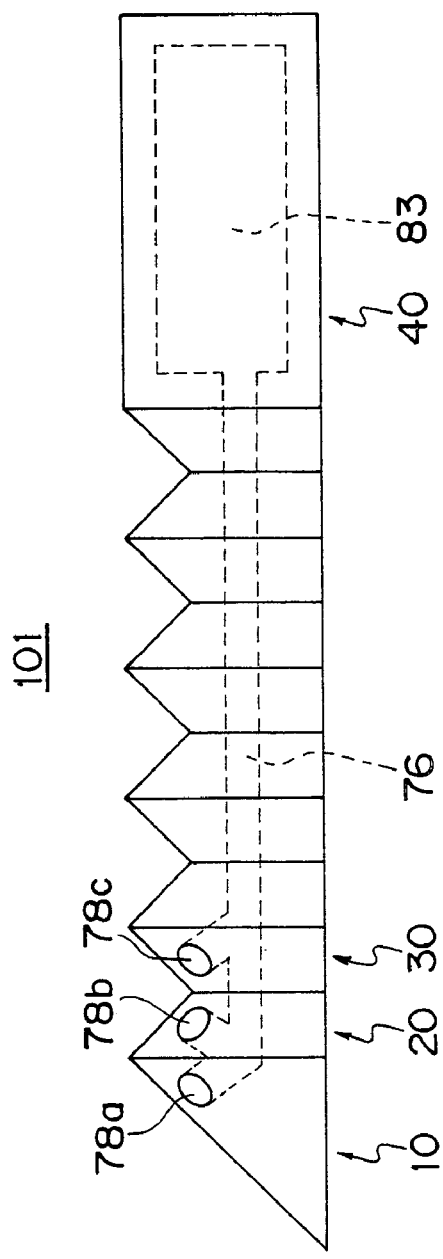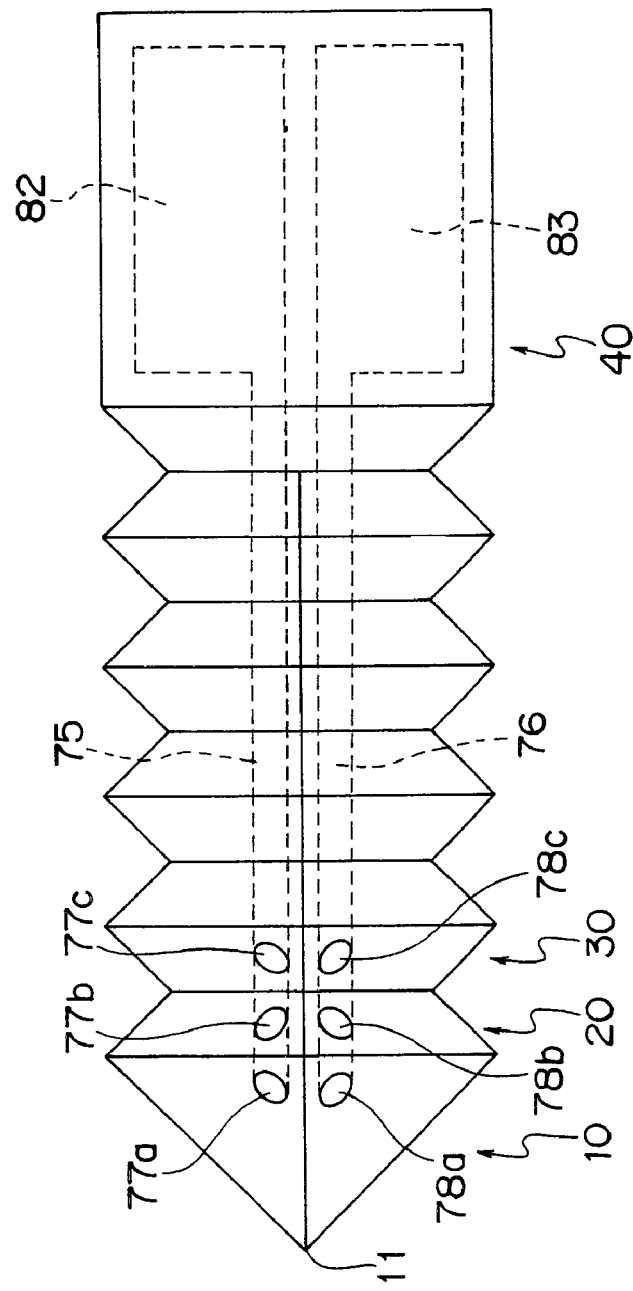
Fig. 13A
Fig. 13B

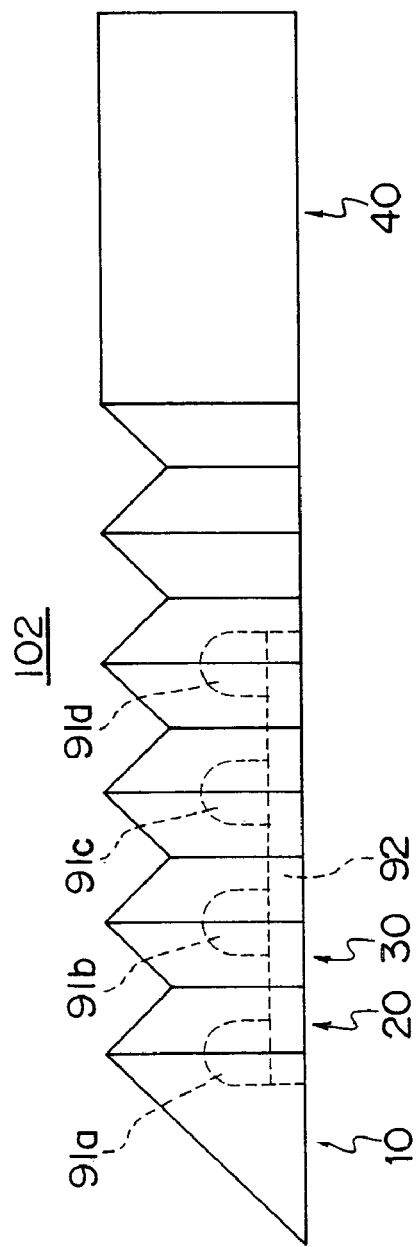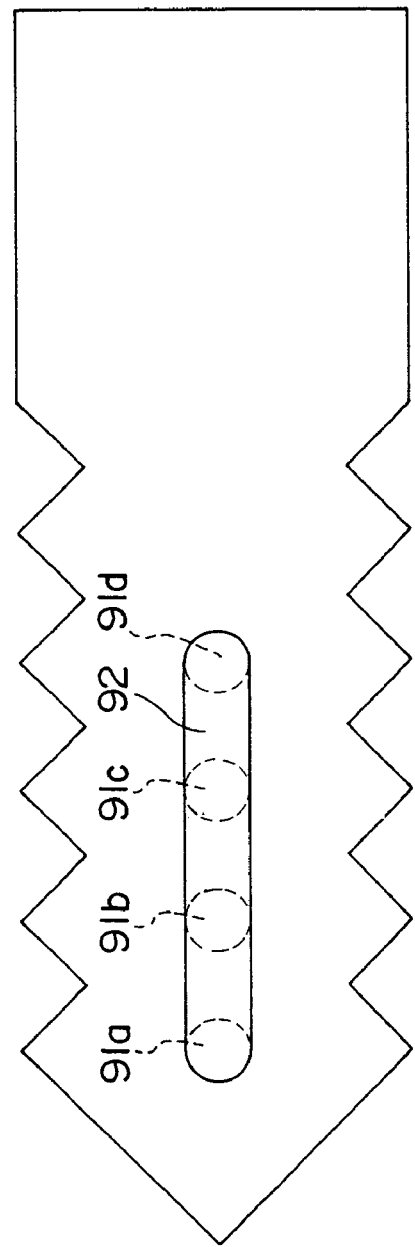
Fig. 14A
Fig. 14B

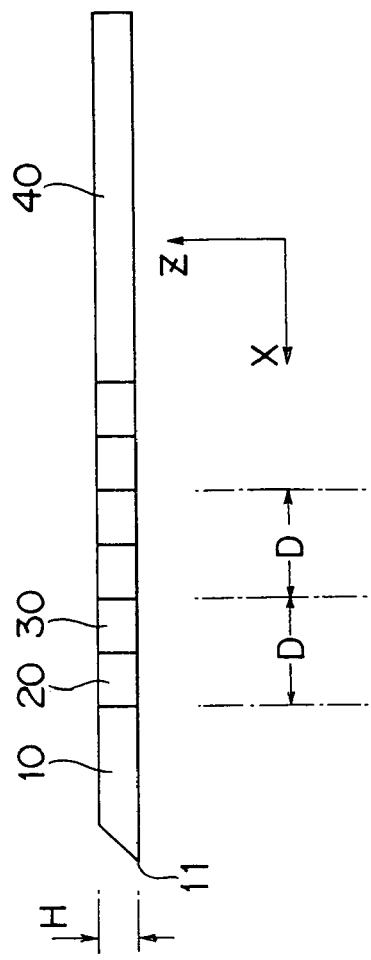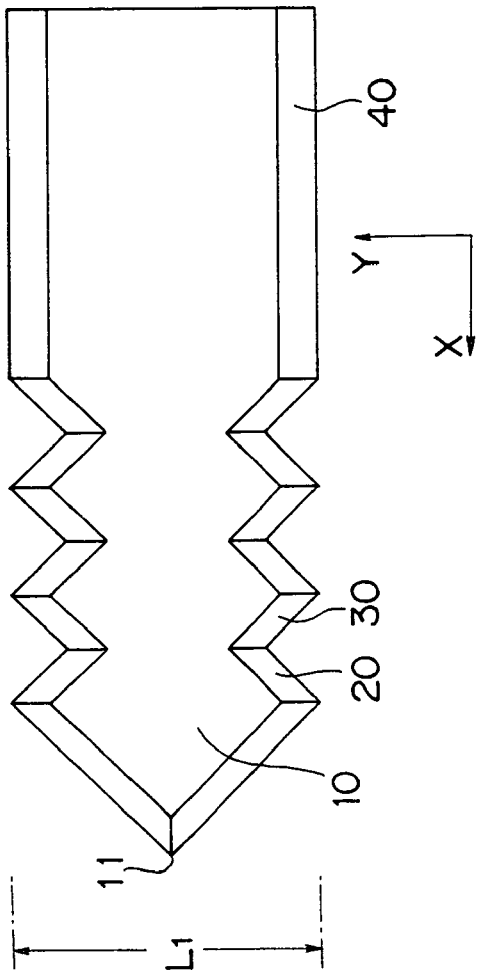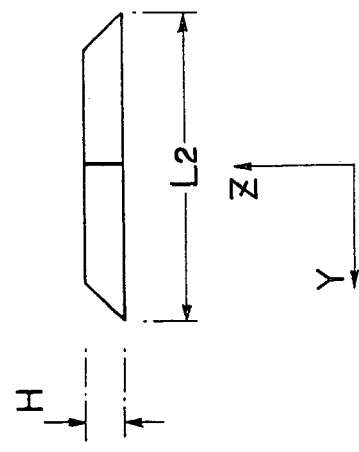

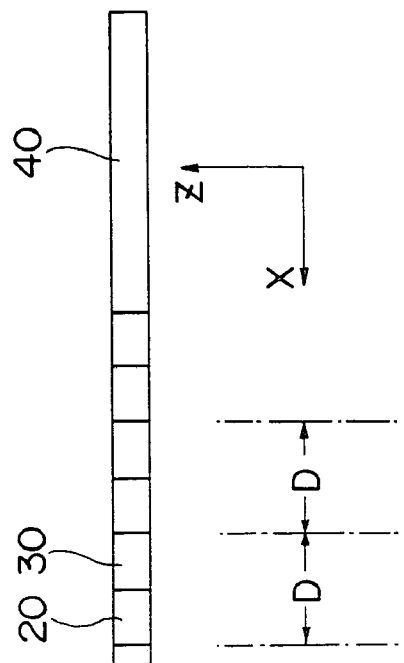
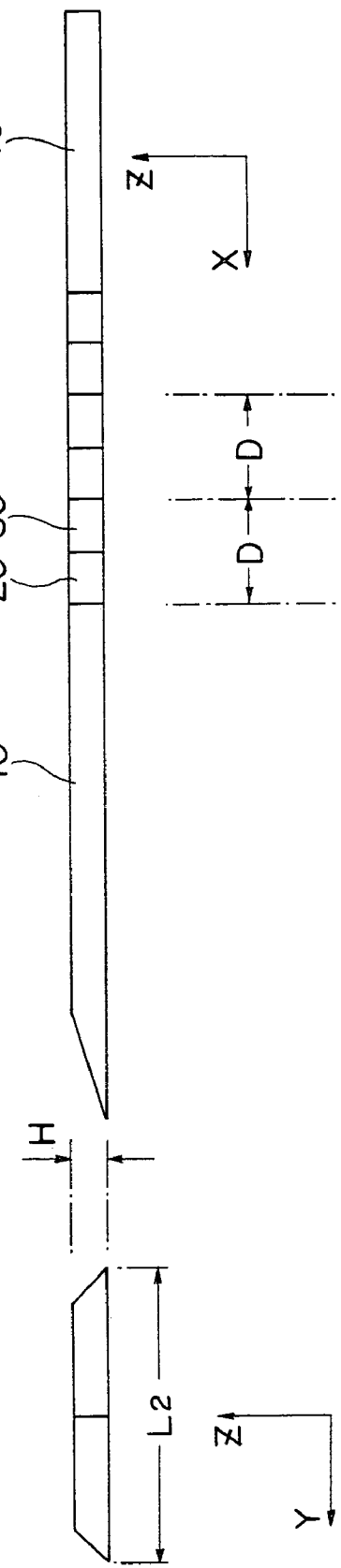
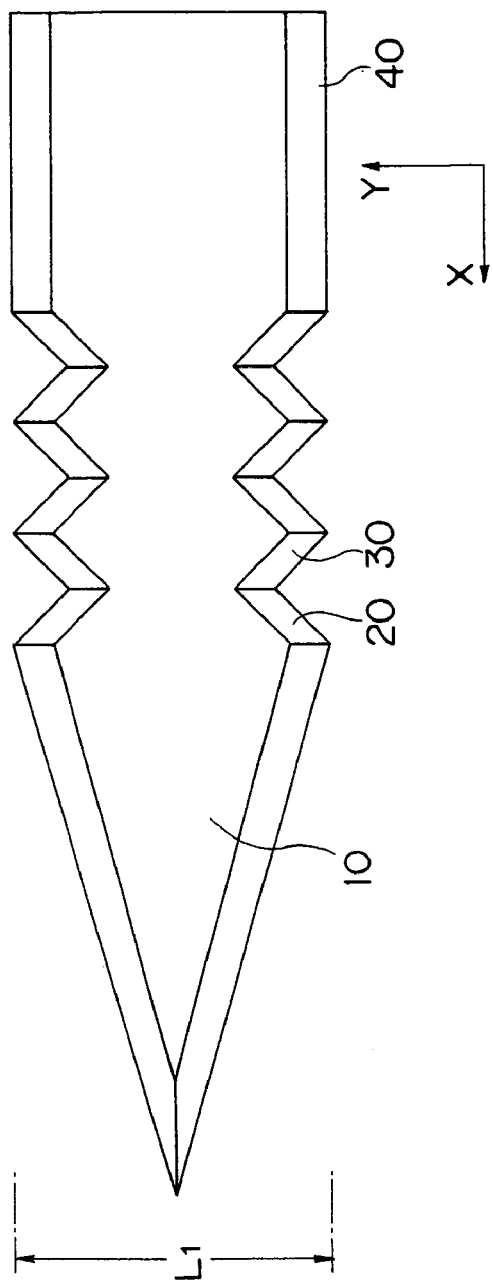

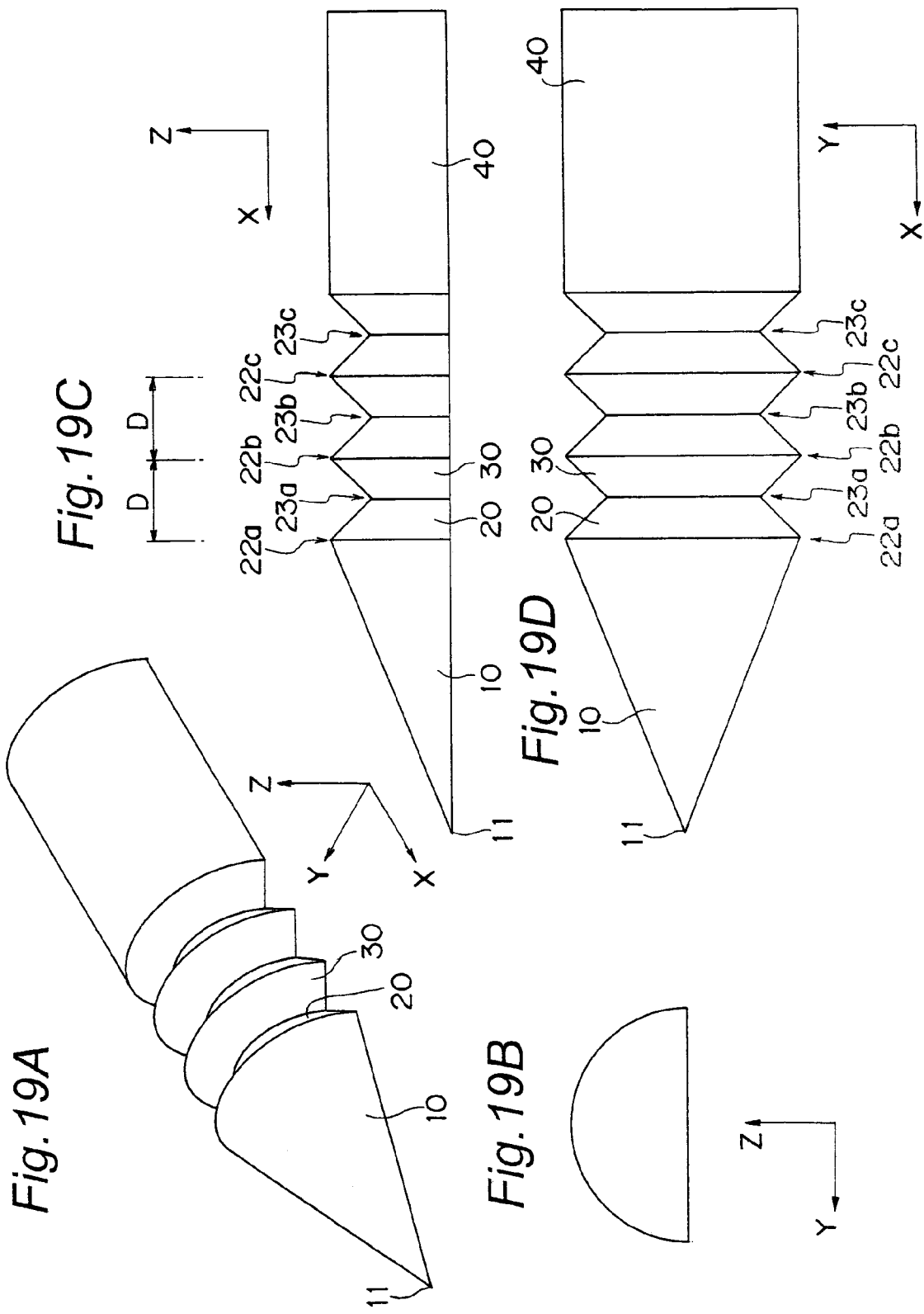

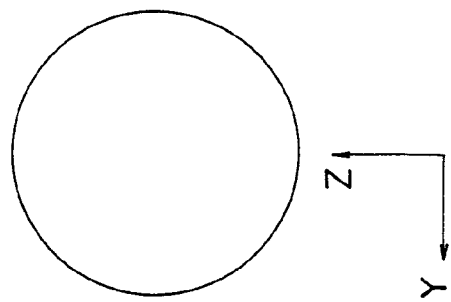
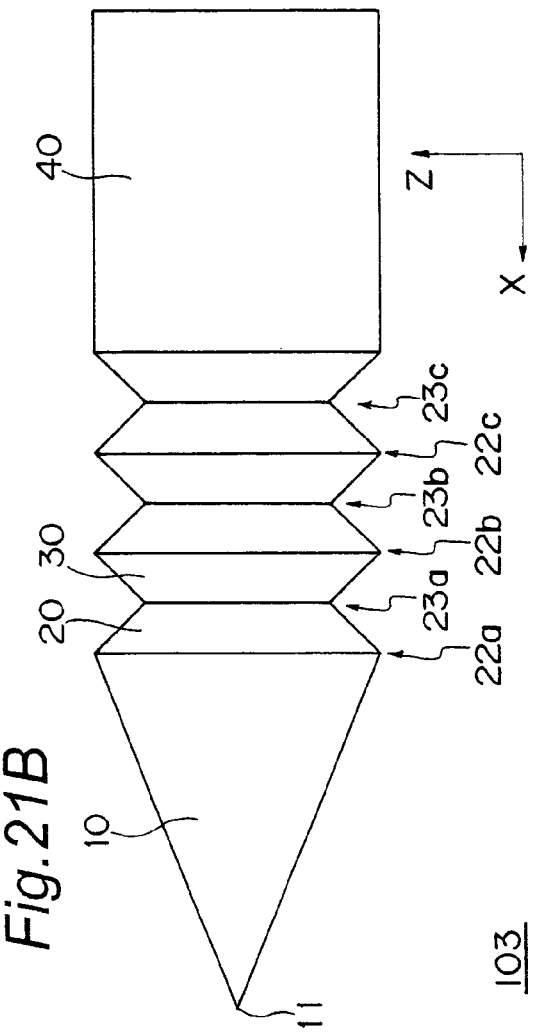
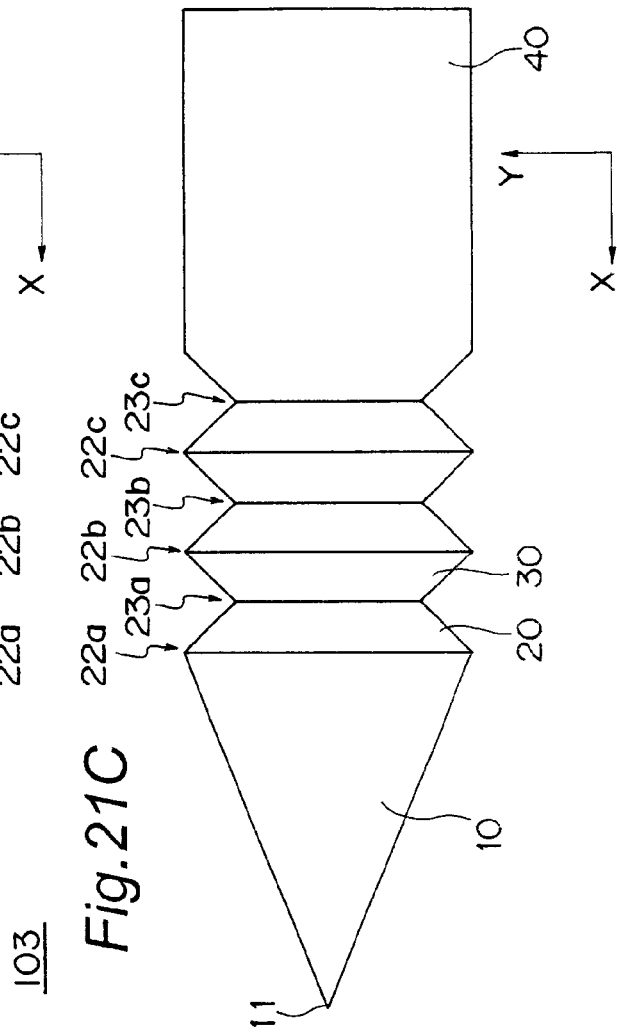

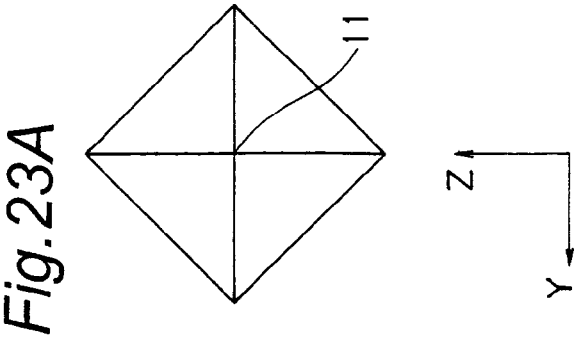
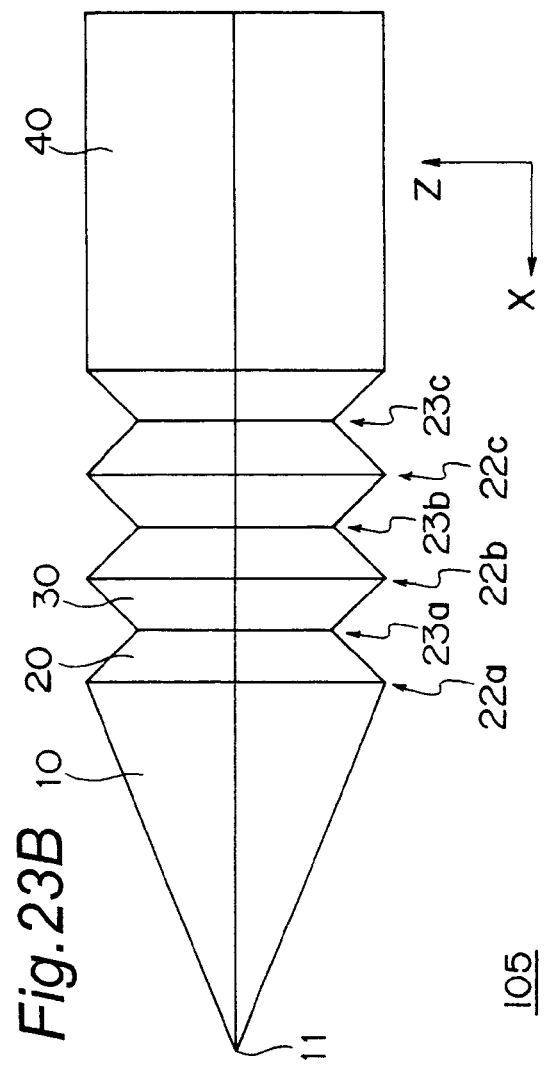
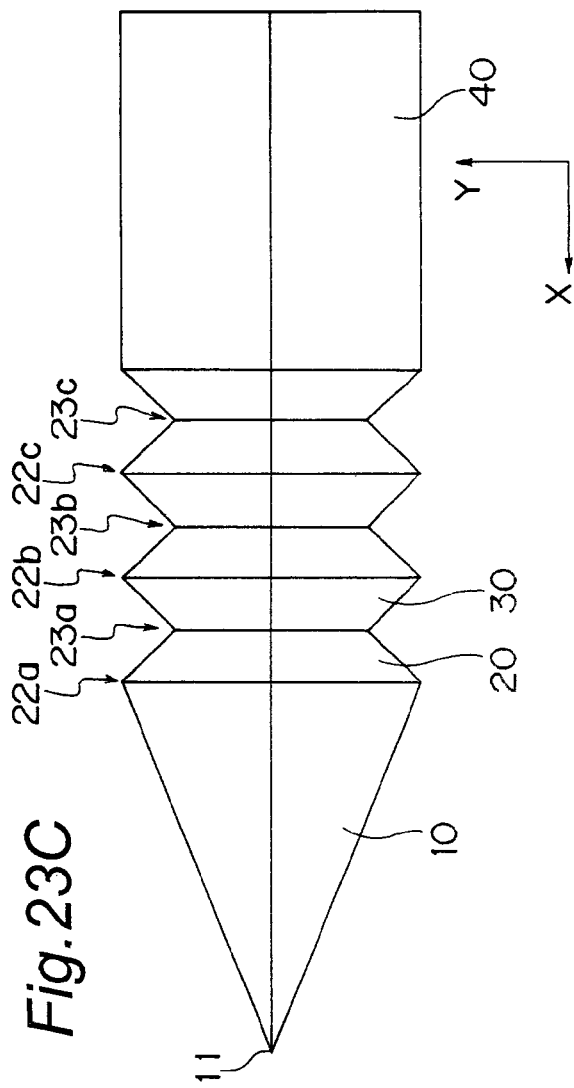

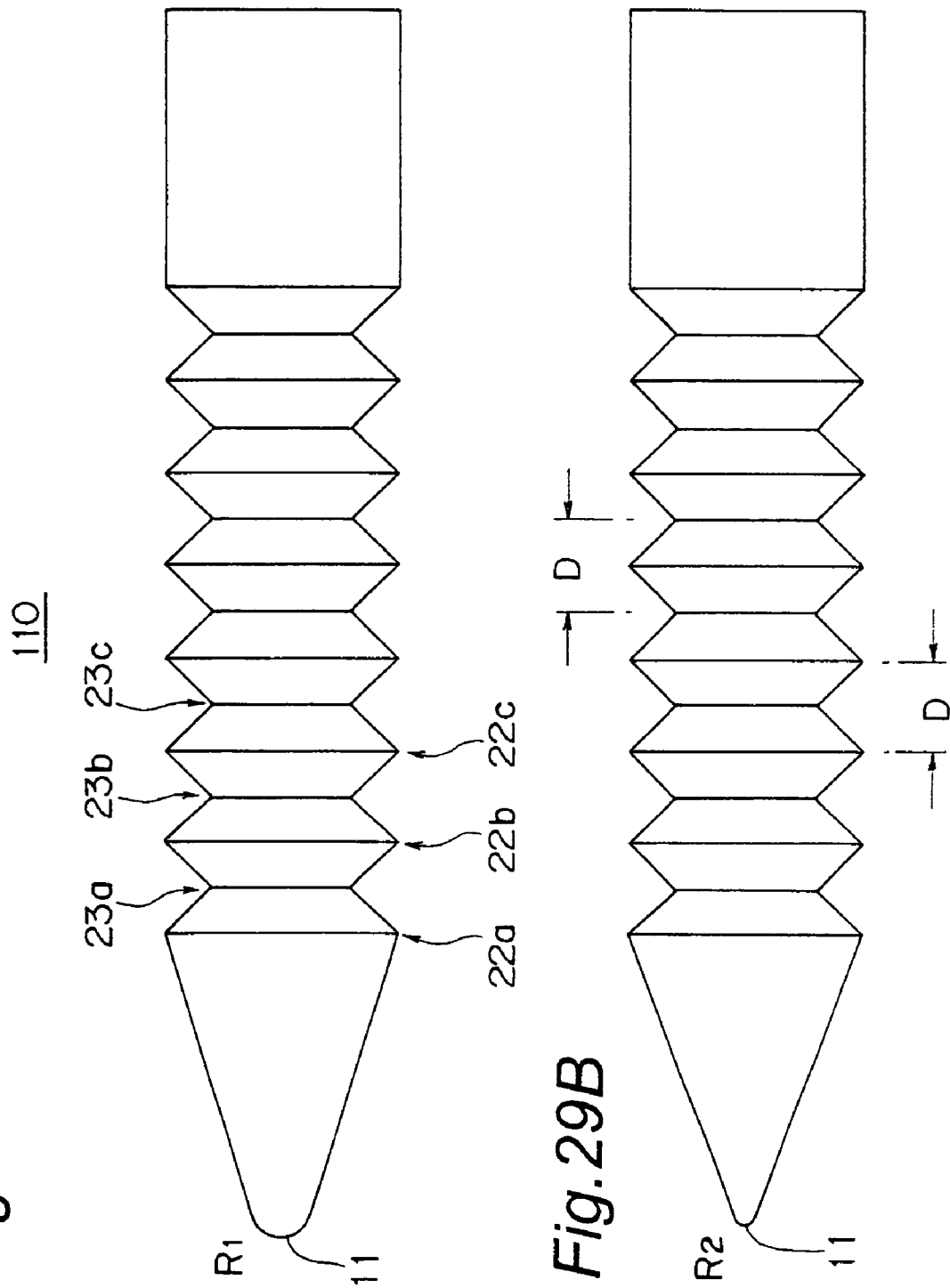

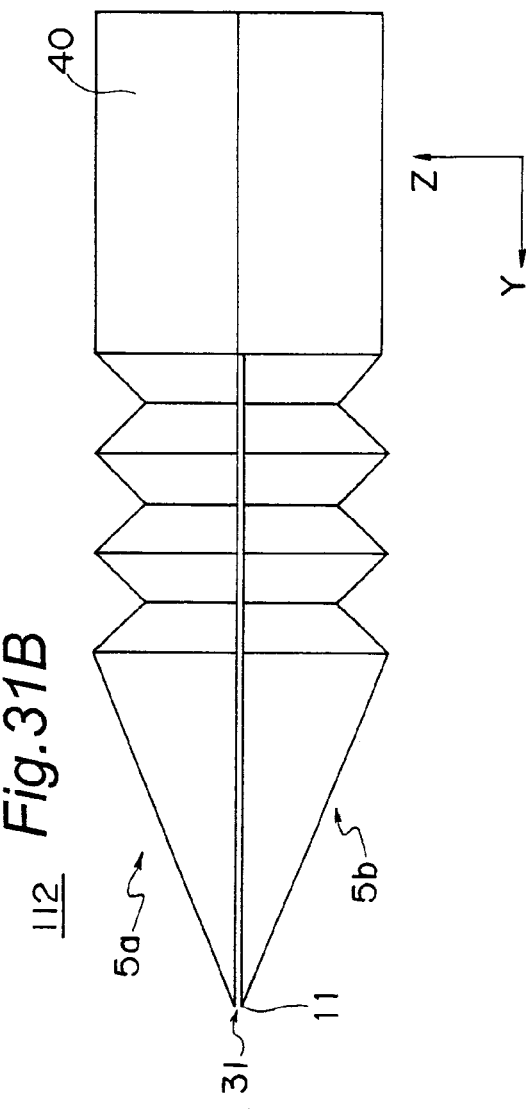
*Fig.31A*
*Fig.31B*
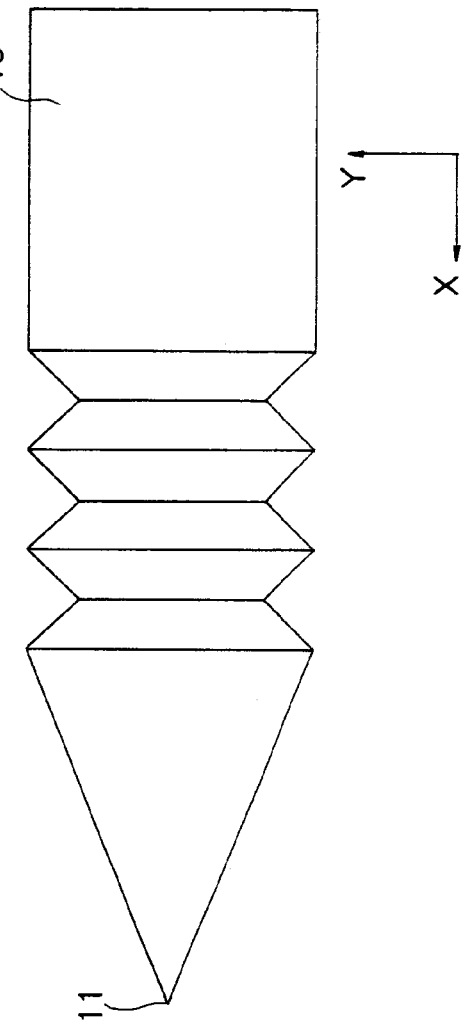
*Fig.31C*

MEDICAL NEEDLE AND MEDICAL DEVICE

TECHNICAL FIELD

The present invention relates to a medical needle such as a lancet and an injection needle and to a medical device using thereof, and in particular, relates to the medical needle made of biocompatible material and to the medical device using thereof.

BACKGROUND ART

In general, when a patient has a hypodermic injection, an injection needle is shot at an appropriate portion of the body such as skin and muscle to inject medicine inside the patient. Also, a diabetic uses a lancet to sample a small amount of his or her blood by stinging it on any suitable portions, e.g., at fingertip, for routine measurement of blood sugar. The patient having such an injection needle or lancet pierced into the body, especially children, sometimes suffers unendurable pain or uncomfortableness. Also, a substantial area of cells around the tingled portion may often be damaged, requiring some time to be healed. Therefore, there has been long-felt desire to develop a less invasive injection needle and lancet, minimizing the pain (unpleasantness) experienced by the patient.

In fact, some of injection needles have been proposed with a little pain to the patient. For example, the Japanese Patent Laid-Open Publication JPA 10-57490 explains the primary reason of the patient's pain that the needle tip "catches" the skin or flesh as the injection needle is penetrating. Also, it discloses a hypodermic injection needle with multi-beveled tip geometry so as to reduce the pain.

Patent Document 1: JPA 10-57490

The present inventors has found the reason of the pain more precisely as described below, and made the invention based upon the knowledge. As the injection needle is penetrating into the tissue such as skin and flesh of the patient, a contacting surface between an outer surface of the injection needle and the tissue of the patient is increased so that the frictional force therebetween becomes greater and the peripheral cells adjacent to the injection needle are drawn inside deeply. To this end, the peripheral cells are extremely deformed by the physical stress due to the frictional force, and may often be burst away (collapsed) so that a pain-producing chemical mediator such as histamine and bradykinin is released within the tissue, thereby hurting the patient. Also, the peripheral cells collapsed by the physical stress extend across the substantial region, which makes more painful and less healable. As described above, the conventional injection needle is highly invasive to pierce the tissue of the patient.

Also, the lancet is used to sample a drop of blood by stinging into the tissue at the appropriate portion of the patient's body. Thus, while there are possible drawbacks as the above-mentioned injection needles, it is highly desired to provide the lancet designed less invasive by minimizing the frictional stress to the peripheral tissue of the patient. According to the medical needle of the present invention, it cuts the peripheral cells as few as possible and wedges away the intact tissues into the deep inside, as will be described herein in detail.

Therefore, one of the aspects of the present invention is to provide a less invasive medical needle giving less pain to the patient.

DISCLOSURE OF INVENTION

The first aspect of the present invention provides a medical needle extending along a predetermined direction and having a vertical cross-section taken along a plane perpendicular to the predetermined direction of which cross-sectional area varies based upon a distance from a needle tip. The medical needle includes a plurality of maximal points where the cross-sectional area of the vertical cross-section is locally maximal, and a plurality of minimal points where the cross-sectional area of the vertical cross-section is locally minimal. The vertical cross-section at the maximal point closest to the needle tip has the cross-sectional area not less than those at any other maximal points.

Preferably, the medical needle further includes at least one channel formed therein extending along the predetermined direction and having at least one opening.

More preferably, the medical needle further includes a holding member connected to a needle rear, and the holding member has at least one chamber in communication with the channel.

Alternatively, the medical needle further includes at least one groove extending along the predetermined direction.

Also, the medical needle further includes a holding member connected to a needle rear, and holding member has at least one chamber in communication with the groove.

Preferably, when viewed on a projected plane parallel to the predetermined direction, the cross-sectional area varies in a linear or curved manner between one of maximal points and the adjacent one of the minimal points.

Preferably, the vertical cross-section has a shape selected from a group consisting of triangle, quadrangle, hexagon, polygon, circle, and ellipse.

Also, the vertical cross-section at the maximal point closer to the needle tip may have the cross-sectional area greater than that at another maximal point closer to the needle rear.

Further, the vertical cross-sections at the minimal points may have the same cross-sectional area to each other.

Even further, the vertical cross-section at the minimal point closer to the needle tip may have the cross-sectional area less than that at another maximal point closer to the needle rear.

Alternatively, the cross-sectional area of the vertical cross-section at the minimal point closest to the needle rear may be less than those at any other minimal points.

Also, a distance between a pair of the adjacent maximal points may be substantially equal to one between another pair of the adjacent maximal points.

Alternatively, a pair of the adjacent maximal points closer to the needle tip may be more spaced than another pair of the adjacent maximal points closer to the needle rear.

Preferably, the medical needle further includes a grating.

Also preferably, the needle tip has a radius of curvature of 10 μm or less.

Further preferably, the medical needle further includes a slit extending along the predetermined direction.

the medical needle is made, preferably of biocompatible material, and more preferably of biodegradable material.

The second aspect of the present invention provides a medical needle of biodegradable material extending along a predetermined direction. The medical needle has a triangular cross-section taken along a plane perpendicular to the predetermined direction of which cross-sectional area varies based upon a distance from a needle tip. Also, it includes a first ascending region of which cross-sectional area monotonically increases as being away from the needle tip, a descending region of which cross-sectional area monotonically decreases as being away from the needle tip, and a second ascending region of which cross-sectional area monotonically increases as being away from the needle tip. The first ascending region, the descending region, and the second ascending region subsequently and integrally formed, and the first and second ascending regions have the largest cross-sections with the largest cross-sectional area having substantially the same size and shape to each other.

Preferably, the medical needle further includes at least one additional descending and ascending regions subsequently and integrally formed of biodegradable material, extending in the predetermined direction. Each of the additional descending and ascending regions has the cross-sectional area which monotonically increases and decreases.

Also preferably, the smallest cross section in the descending region is similar to the largest cross section in the ascending regions, and the smallest cross section in the descending region has the area greater than one-fourth of the area of the largest cross section in the ascending regions. More preferably, the smallest cross section in the descending region has the area greater than four-ninths of the area of the largest cross section in the ascending regions. Further, the largest cross sections in the first and second ascending regions are spaced away from each other by a gap greater than one 1 μm.

Also preferably, the lancet further includes a constant region integrally formed of biodegradable material between the descending region and the second ascending region, having triangular cross sections taken along any planes perpendicular to the predetermined direction, of which area is constant.

Preferably, the area of the triangular cross sections in the first and second ascending regions are linearly increased at first and second increasing rates, respectively, and the first increasing rate falling within a range between one-sixteenth and one of the second increasing rate. More preferably, the first increasing rate is one-ninth of the second increasing rate.

The medical needle may further include a holding region of biodegradable material connected to the second ascending region.

Preferably, the medical needle further includes at least one channel extending in the predetermined direction through at least one of the first and second ascending regions and descending region. Also, the holding region has at least one chamber in communication with the channel. The channel has at least one opening. Preferably, the channel has at least two openings spaced away from each other by a predetermined gap. More preferably, a plurality of the channels are provided, and the holding region has a plurality of the chambers, each of the chambers being in communication with corresponding one of the channels. Alternatively, the medical needle further includes at least one groove extending in the predetermined direction through at least one of the first and second ascending regions and descending region.

Further, the medical needle further includes a plurality of vertical cavities extending in a vertical direction perpendicular to the predetermined direction, and a seal membrane of biodegradable material for sealing the vertical cavities. The seal membrane has the thickness in the vertical direction varying based upon the position of each of the vertical cavities.

The third aspect of the present invention provides a medical needle including a first ascending region, a descending region, and a second ascending region subsequently and integrally formed of biodegradable material. Those regions extend from a needle tip in a predetermined direction, each of the regions having trapezoidal cross sections taken along any planes perpendicular to the predetermined direction. The first and second ascending regions have the trapezoidal cross sections of which base monotonically increases as being away from the needle tip. The descending region has the trapezoidal cross sections of which base monotonically decreases as being away from the needle tip. The first and second ascending regions have the largest cross section having substantially the same size and shape to each other.

Also, the medical needle further includes at least one additional descending and ascending regions subsequently and integrally formed of biodegradable material, extending in the predetermined direction.

Preferably, the smallest cross section in the descending region has the base greater than a half of the base of the largest cross section in the ascending regions. More preferably, the smallest cross section in the descending region has the base greater than two-thirds of the base of the largest cross section in the ascending regions. Further preferably, the largest cross sections in the first and second ascending regions are spaced away from each other by a gap greater than one micron. Further, a continuous curved portion is provided between the descending region and the second ascending region.

Also, the medical needle preferably further includes a constant region integrally formed of biodegradable material between the descending region and the second ascending region.

Preferably, the base of the trapezoidal cross sections in the first and second ascending regions are linearly increased at first and second increasing rates, respectively, and the first increasing rate falling within a range between one-fourth and one of the second increasing rate. More preferably, the first increasing rate is one-third of the second increasing rate.

The medical needle may further include a holding region of biodegradable material connected to the needle rear.

The fourth aspect of the present invention provides a medical needle extending along a predetermined direction and having a vertical cross-section taken along a plane perpendicular to the predetermined direction of which cross-sectional area varies based upon a distance from a needle tip. The medical needle includes a plurality of maximal points where the cross-sectional area of the vertical cross-section is locally maximal, and a plurality of minimal points where the cross-sectional area of the vertical cross-section is locally minimal. The vertical cross-section at the maximal point closest to the needle tip has the cross-sectional area not less than those at any other maximal points.

ADVANTAGE OF INVENTION

A medical needle according to one of the aspects of the present invention reduces pain to the patient and minimizes damage to the pierced portion of the patient.

BRIEF DESCRIPTION OF DRAWINGS

FIGS. 9A-9C are front elevational, side, and top plan views of the lancet shown in FIG. 8, respectively.

FIGS. 11A-11C are side, top, and rear elevational views of the lancet of the first modification.

FIGS. 12A and 12B are side and bottom views of another lancet of the first modification.

FIGS. 13A and 13B are side and top plan views of further another lancet of the first modification.

FIGS. 14A and 14B are side and bottom views of a lancet of the second modification.

FIG. 17A-17C are front elevational, side, and top plan views of the lancet shown in FIG. 15A, respectively.

FIGS. 18A-18C are front elevational, side, and top plan views of the lancet shown in FIG. 15B, respectively.

FIG. 19A-19D are perspective, front elevational, side, and top plan views of the lancet according to the fifth embodiment of the present invention.

FIGS. 21A-21C are front elevational, side, and top plan views of the lancet according to the third modification of the fifth embodiment.

FIGS. 23A-23C are front elevational, side, and top plan views of the lancet according to the fifth modification of the fifth embodiment.

FIGS. 29A-29B are top plan views of the lancet according to the tenth modification of the above embodiments.

FIGS. 31A-31C are front elevational, side, and top plan views of the lancet according to the twelfth modification of the above embodiments.

Figure 1:
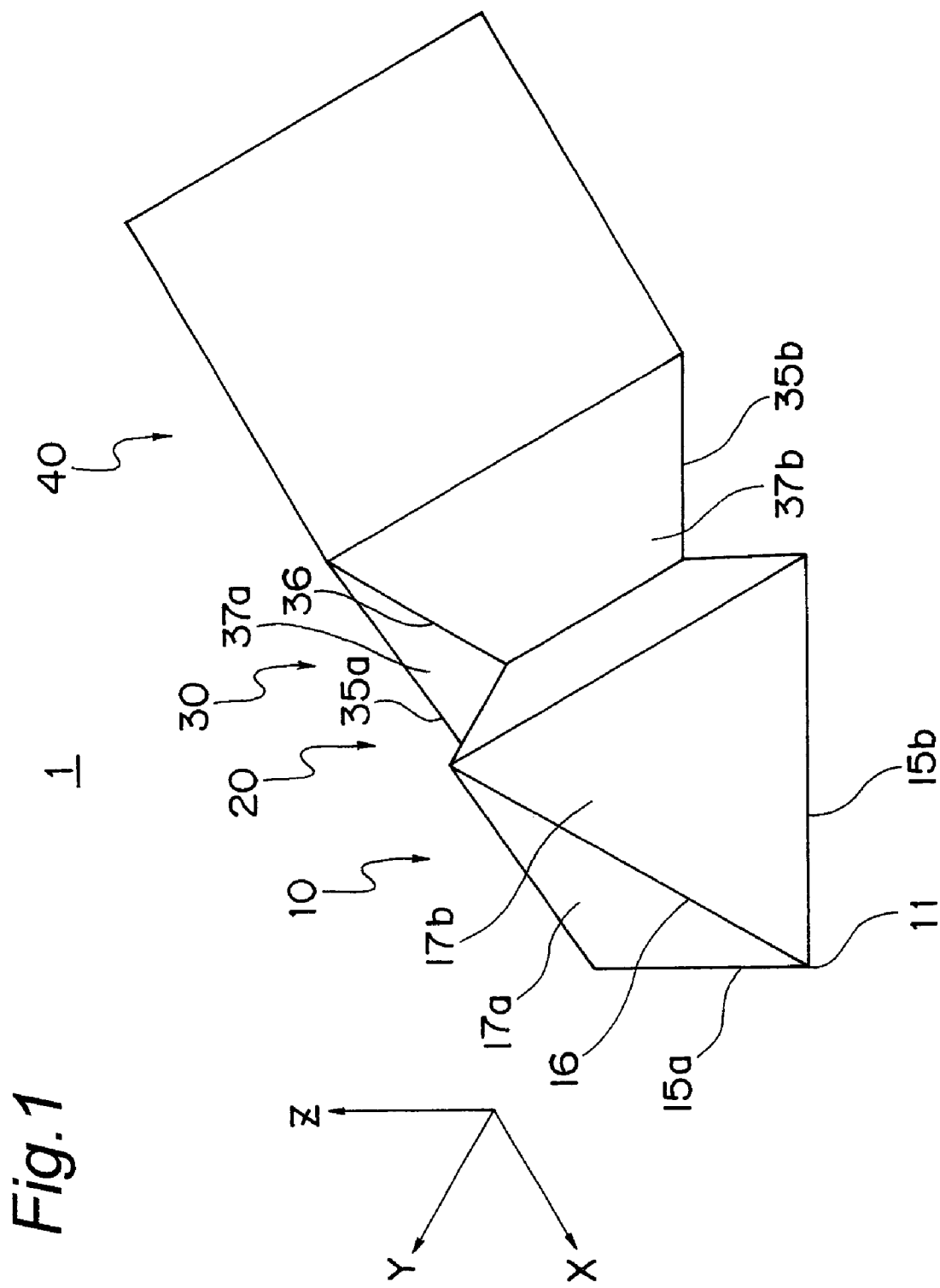
FIG. 1 is a perspective view of a lancet according to the first embodiment of the present invention.

DENOTATION OF REFERENCE NUMERALS 1-6, 101-112 lancet; 10 first ascending region (first tissue incising region); 11 tip; 12 first diagonal; 13 second diagonal; 14 bottom surface; 15a-15c, 16 member (sharp ridge lines); 17a, 17b side surface; 18 rear end portion; 20 first descending region (first friction releasing region); 21 side surface; 22a-22c local maximum point; 23a-23c local minimum point; 24 grating; 25 peak; 26 slope surface; 27 blood; 28 incident beam; 29 reflected beam; 30 second ascending region (second tissue incising region); 37a, 37b side surface; 40 holding region; 51-53, Y-Z plane; 60a, 60b constant region; 71, 75, 76 channel; 72 opening; 73 bottom surface; 74 groove; 75, 76 channel; 77, 78 opening; 81-83, chamber; 91 vertical hole; 92 sealing member.

BEST MODE FOR CARRYING OUT THE INVENTION

Referring to the attached drawings, various embodiments of a medical needle according to the present invention will be described hereinafter. Among them, in particular, a solid type of a lancet will generally be discussed as an example just for clear understandings. Therefore, although not described in detail, it should be noted that the present invention can equally be applied to a solid type of a medical needle as well.

Also, in the description of each embodiment, although the terminology indicating the directions (for example, "X-direction", "Y-direction", and "Z-direction") are conveniently used just for facilitating easy understandings, it should not be interpreted that those terminology limit the scope of the present invention.

Embodiment 1

With reference to FIGS. 1 to 4, the first embodiment of the lancet according to the present invention will be described herein. The lancet 1 is used to sample a drop of blood of a patient such as a diabetic for measurement of blood sugar by stinging it onto the appropriate portion (e.g., fingertip) of the patient's body. As illustrated in FIGS. 1 and 2, the lancet 1 extends along the X-direction and has a triangle cross-section as taken along any Y-Z planes. The triangle cross-section includes a base, height, and area varying in accordance with the distance from a lancet tip 11 or the position of the X-axis. Thus, the lancet 1 includes a first ascending region (first tissue incising region) 10 of which area is monotonically increased as being away from the tip 11, a first descending region (first friction releasing region) 20 of which area is monotonically decreased as being away from the tip 11, and a second ascending region (second tissue incising region) 30. A holding region 40 is connected to the second ascending region 30 of the lancet 1.

In other words, as illustrated in FIG. 1, the lancet 1 of the present invention extends along a predetermined direction (X-direction) and has a cross-section (referred to as a "vertical cross-section" herein) taken along a plane perpendicular to the predetermined direction of which cross-sectional area varies based upon a distance from a needle tip 11. The lancet 1 includes a plurality of maximal points (Y-Z planes 51, 53) where the cross-sectional area of the vertical cross section is locally maximal, and a minimal point (Y-Z plane 52) where the cross-sectional area of the vertical cross section is locally minimal. Also, it is designed such that the cross-sectional area of the vertical cross-section at the maximal point closest to the needle tip is the same as those at any other maximal points.

In general, the lancet 1 of the present invention is formed of any biocompatible materials including polymer macromolecule, bio-macromolecule, protein, and biocompatible inorganic material.

The polymer macromolecule includes for example, although not limited thereto, polyvinylchloride, polyethyleneglycol, parylene, polyethylene, polypropylene, polydimethylsiloxane (silicone), polyisoprene, polymethylmethacrylate, polytetrafluoroethylene, polyetherimide, poly(ethylene oxide), polyethyleneterephthalate, polyethylenesuccinate, polybuthyleneterephthalete, polybuthylenesuccinate, poly (buthylenesuccinatecarbonate), poly(phenylene oxide), polyphenylene sufide, polyformaldehyde, polyanhydride, polyamide (6-nyron, 6,6-nyron), polybutadiene, polyvinylacetate, polyvinylalcohol, polyvinylpyrrolidone, polyesteramide, copolymer of MMA, polyacrylonitrile, polysulfone, polyethersulfone, copolymer of styrene, polycarbonate, polyurethane(polyetherurethane, polyesterurethane, polyureaetherurethane), polyvinylidenefluoride, polystyrene, acetal resin, polybutadiene, ethylene-vinylacetate copolymer, ethylene-vinylalcohol-copolymer, ethylene propylene copolymer, poly(hydroxyethylmethacrylate), polyhydroxybutyrate, polyorthoester, polylactide, polyglycolide, polycaprolactone, copolymer of glycolide and lactide, polydioxanone, perfluoroethylenepropylene copolymer, polybutylcyanoacrylate, polyaryletherketone, epoxy resin, polyester resin, polyimide, phenolic resin and etc.

The bio-macromolecule includes for example, although not limited thereto, cellulose, amylum, chitin, chitosan, gelatin, carrageenan, alginic acid, agarose, pullulan, mannan, curdlan, xanthan gum, gellan gum, pectin, xyloglucan, cyamoposis gum, lignin, oligosaccharide, hyaluronic acid, schizophyllan, lentinan, and etc. The protein includes for example, although not limited thereto, collagen, gelatin, keratin, fibroin, glue, sericin, botanical protein, milk protein, egg protein, composite protein, heparin, nucleic acid, and etc. Also, sugar, candy, glucose, maltose, sucrose, and polymer alloy thereof may be used therefor.

The biocompatible inorganic material includes for example, although not limited thereto, ceramics, nano-composites ceramics, $Al_2O_3/ZnO_2$ composites ceramics, $Si_3N_4$-based nano-composite material, apatite hydroxide, calcium carbonate, carbon, graphite (nano-grafiber), carbon nano-tube (CNT), fullerene composite material, hydroxy-apatite polymer-composite material, cobalt-chrome alloy stainless, and etc.

However, preferably, the lancet 1 of the present invention is integrally formed of biodegradable material including for example, poly lactic acid, poly glycolic acid, poly caprolactone, collagen, amylum, hyaluronic acid, alginic acid, chitin, chitosan, cellulose, gelatin, and the compound/composition/copolymer/poly-microparticle thereof.

In general, after such an injection needle and lancet are once used and then disposed immediately without reused, to prevent various infections. Also, they are usually treated as industrial waste for landfill rather than as the burnable waste. Meantime, in case where the lancet 1 made of biodegradable material such as poly lactic acid is landfilled, advantageously, it is degraded into water and carbon dioxide by microorganism within the soil. Therefore, the lancet 1 made of biodegradable material is better and safer not only for the ecology but also for the patient since even if a portion of the lancet is broken off and remained in the patient's body, it will also be easily degraded within the body.

Next, referring to FIGS. 2A to 2C, the structure of the regions 10, 20, 30 composing the lancet 1 will be described in more detail. Each of the first and second ascending regions 10, 30 and the first descending region 20 has an outer configuration registered with the respective portion of a particular rectangle pyramid.

Figure 2A:
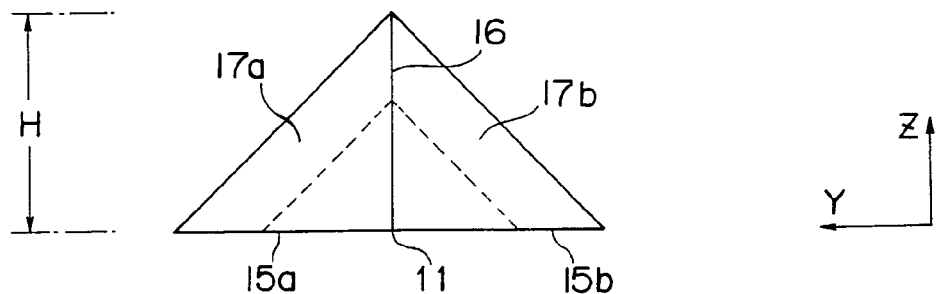
FIGS. 2A-2C are front elevational, side, and top plan views of the lancet shown in FIG. 1, respectively.
Figure 2B:
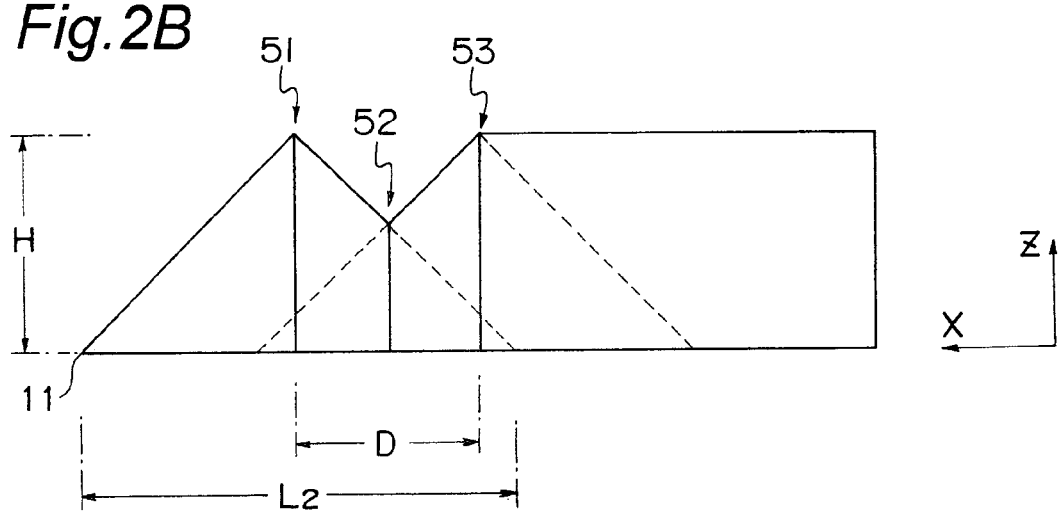
Figure 2C:
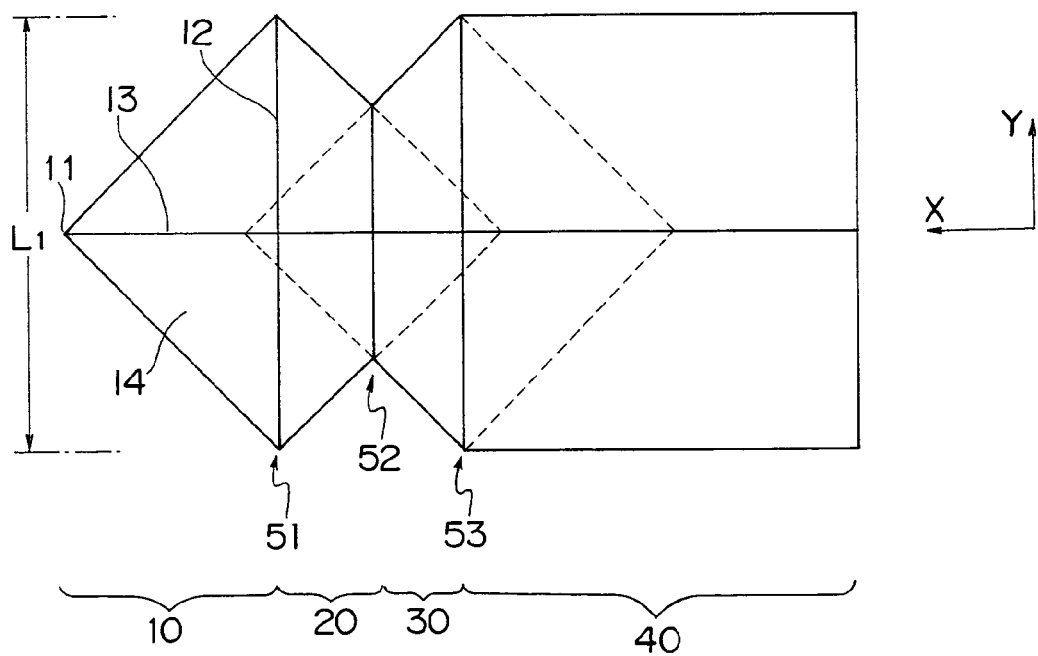

The rectangle pyramid has a predetermined height (H) as shown in FIGS. 2A and 2B, and a rhombic base 14 having first and second predetermined diagonals 12 ($L_1$), 13 ($L_2$), respectively. Preferably, the base is shaped as a square so that the first and second diagonals 12, 13 have the same length ($L_1=L_2$). Further, the height of the rectangle pyramid has a half of the length of the first and second diagonals 12, 13 ($H=L_1/2=L_2/2$), where the side surface (e.g., 17a, 17b) of the rectangle pyramid has a shape of an equilateral triangle.

In particular, the first ascending region 10 has an outer configuration registered with a first portion of the particular rectangle pyramid taken along the Y-Z plane 51 as shown in FIG. 2B. The first descending region 20 has an outer configuration registered with a second portion of the rectangle pyramid taken along and between the Y-Z planes 51 and 52. Also, the second ascending region 30 has an outer configuration registered with a third portion of the rectangle pyramid taken along and between the Y-Z planes 52 and 53. As above, those regions 10, 20, 30 of the lancet 1 are integrally formed such that each of the regions includes a base surface arranged on the same X-Y plane and the second diagonal arranged on the same line along the x-axis. It should be noted that each of the rectangle pyramid configuring the respective region has substantial the same dimension.

In the lancet 1 so structured, the cross-sections taken along any Y-Z planes are triangle and include a base, a height, and an area lineally increasing or decreasing depending upon the distance from a lancet tip 11 or the position of the X-axis. In the above description, the increase and decrease in size of the regions 10, 20, 30 are explained as being linear functions of the distance from the lancet tip 11 or the position along the x-axis. However, it should be noted that the base, the height, and the area of the cross-section in those regions may be defined as any non-linear functions such as a second or higher order functions which monotonically increases or decreases. Thus, the base, the height, and the area of the regions can be described by a linear or non-linear function monotonically increasing or decreasing as the parameter of the position along the x-axis.

According to the first embodiment of the present invention, the largest cross-sections in the first and second ascending regions 10, 30 having the maximal cross-sectional area (i.e., the cross-sections taken along the Y-Z planes 51 and 53) has triangular shapes, which are congruent with each other and similar to the smallest cross-section in the first descending regions 20 having the minimal cross-sectional area (i.e., the cross-section taken along the Y-Z plane 52).

Figure 3:
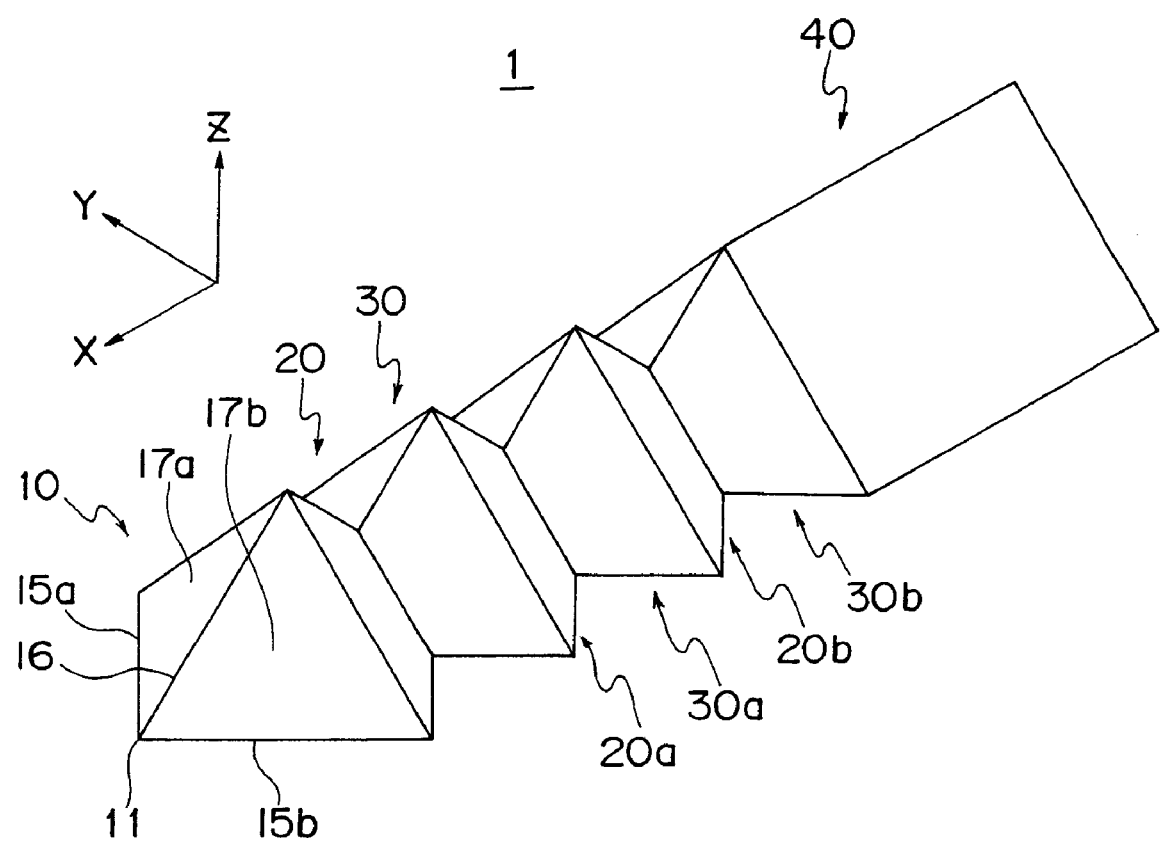
FIG. 3 is a perspective view of another lancet according to the first embodiment.
Figure 4C:
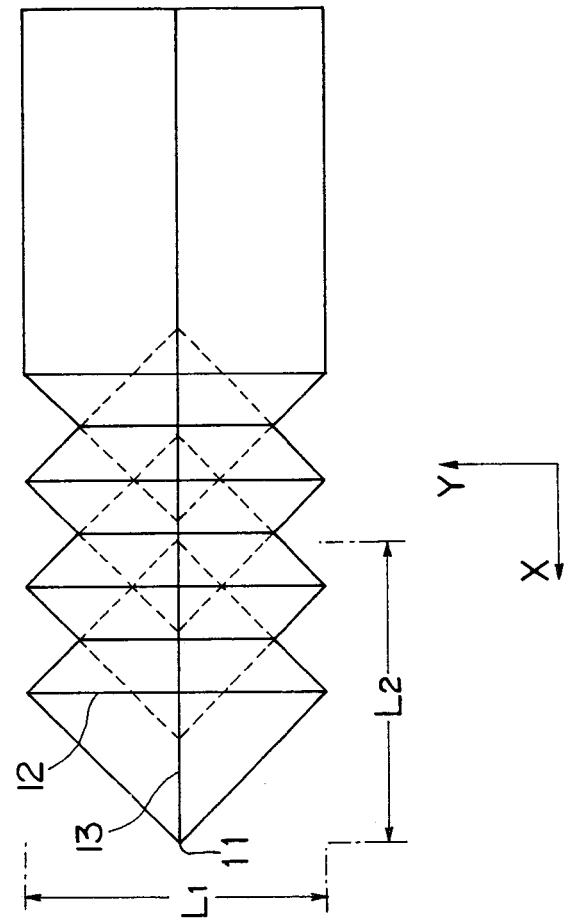
FIGS. 4A-4C are front elevational, side, and top plan views of the lancet shown in FIG. 3, respectively.
Figure 4B:
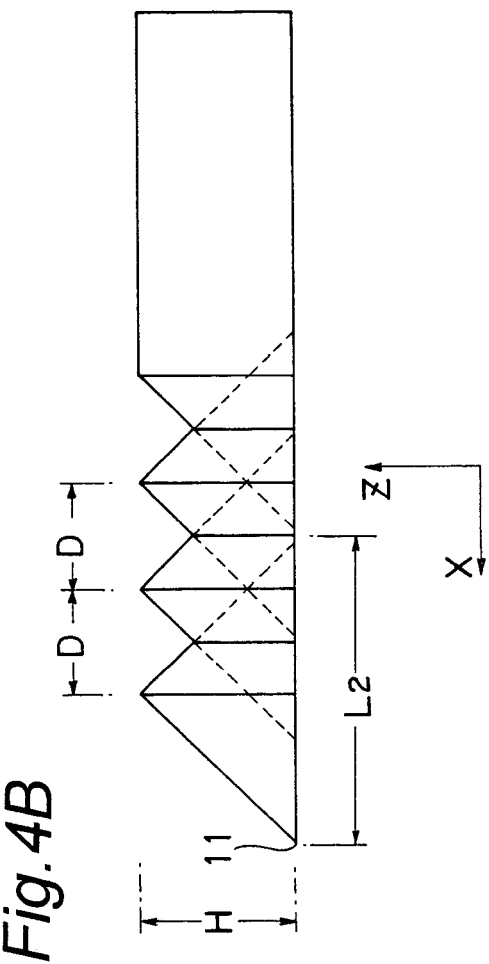
Figure 4A:
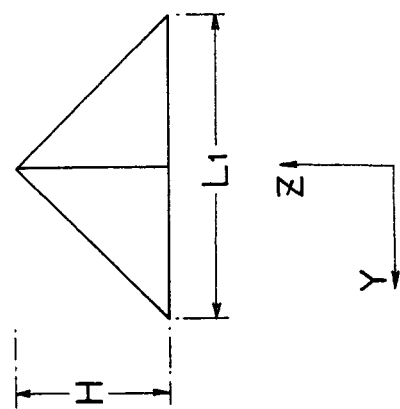

Preferably, the lancet 1 of the first embodiment includes at least one additional descending region 20a, 20b and the ascending region 30a, 30b, as shown in FIGS. 3 and 4. In the additional ascending region 30a, 30b, the largest cross-sections having the maximal cross-sectional area also have substantially the same shape and size as those of the other largest cross-sections.

According to the lancet 1 illustrated in FIGS. 1 to 3, when being penetrated deeply inside the tissue (skin or flesh) of the patient's body, firstly, three of the members (sharp ridge lines) 15a, 15b, 15c of the rectangle pyramid incise the peripheral cells around the tip 11 of the first ascending region (first tissue incising region) 10. Then, the bottom surface 14 and the side surfaces 17a, 17b of the first ascending region 10 wedge away the intact (non-incised) tissues into the deep inside. Thus, the first incising region 10 cuts and advances into the peripheral cells in a smooth manner. As the first incising region 10 advances into the tissue, the frictional force is increased between the surfaces 14, 17a, 17b of the first incising region 10 and the peripheral tissue, so that the peripheral tissue may be drawn into the deep inside by the increased frictional force.

However, after the first incising region 10 sinks within the tissue, and as the lancet 1 is further penetrated inside the tissue, the frictional force between the peripheral tissue and first descending region (first friction releasing region) 20 is released since the first friction releasing region 20 has the cross-section reducing or shrinking in size as being away from the tip 11. Once the frictional force with the first incising region 10 is released, the peripheral tissue drawn inside by the frictional force will be released to the normal position by its elasticity. Thus, the peripheral tissue drawn by the first incising region 10 is returned to the original state so that the physical stress applied to the peripheral cells is reduced or minimized. Therefore, when the lancet 1 is penetrated into the tissue by the half length ($L_1/2$) of the second diagonal of the rectangle pyramid, the peripheral cells drawn inside are released from the frictional force to be replaced, thereby preventing the peripheral cells from being collapsed. This minimizes the pain-producing chemical mediator to give substantially less pain to the patient, and avoids the unrecoverable damage (collapse) to the peripheral cells across a substantial area around the tip 11.

Again, after the first releasing region 20 sinks within the tissue, and as the lancet 1 further advances deeply inside the tissue, three of the members 35a, 35b, 35c of the second ascending region 30 incise substantially the same peripheral cells as the first ascending region cuts. Also, the bottom surface and the side surfaces 37a, 37b of the second ascending region 30 get the intact (non-incised) tissues out of the way, avoiding the unrecoverable damage to the peripheral cells. As above, since the largest cross-sections of the first and second ascending regions 10, 30 are congruent with each other having substantially the same size and shape, the number of the incised cells can be minimized when the lancet 1 is penetrating inside the patient's body.

Thus, the penetrating process of the lancet 1 according to the present invention is achieved by repeatedly incising the peripheral cells and wedging away the intact tissues by the ascending regions 10, 30, and releasing the frictional force with the peripheral cells by the descending region 20 to replace thereof in its original position. Also, the present invention provides a non-invasive lancet 1 minimizing the pain to the patient by returning the peripheral cells across the substantial area back to the original position and by avoiding the damage of the peripheral cells.

Meanwhile, although depending upon the portion of patient's body to be pierced, one of the peripheral cells has a size of about 10 µm in general, and in particular, the microcyte in the micro-vessel has the size of 5 µm. The rectangle pyramid is designed so as to have the first and second diagonals ($L_1$, $L_2$) and the height (H) of about 85 to 180 µm and about 42.5 to 90 µm, respectively. Thus, the largest cross-section in the ascending regions 10, 30 has a triangle shape having a base of about 85 to 180 µm and a height of about 42.5 to 90 µm.

When the base and the height of the smallest cross-section taken along the Y-Z plane 52 are approximately less than a half of those of the largest cross-section taken along the Y-Z planes 51, 53, the lancet 1 has insufficient strength so that it tends to break off between the descending region 20 and the second ascending region 30. Thus, if the base and the height of the smallest cross-section are approximately less than about 42.5 to 90 µm and about 21.2 to 45 µm, respectively, then the lancet 1 is easily broken off. Therefore, the lancet 1 of the embodiment is designed such that the base and the height of the smallest cross-section are approximately greater than a half of those of the largest cross-section, and thus the smallest cross-section is approximately greater than a quarter (square of a half) of the largest cross-section. More preferably, the lancet 1 is designed such that the base and the height of the smallest cross-section is approximately greater than two-thirds (⅔) of those of the largest cross-section, and thus the smallest cross-section is approximately greater than four-ninths (4/9: square of ⅔) of the largest cross-section. This realizes a stubborn and reliable lancet 1 without breaking off and/or bending so as to secure piercing into the patient's body.

Also, the descending region 20 should have the size for releasing the frictional stress of the peripheral cells, i.e., the size of at least one cell, thus as illustrated in FIG. 2A, the gap (D) between the adjacent largest cross-sections taken along the Y-Z planes 51 and 53 is designed to have at least one (1) micron and preferably five (5) microns.

Figure 5A:
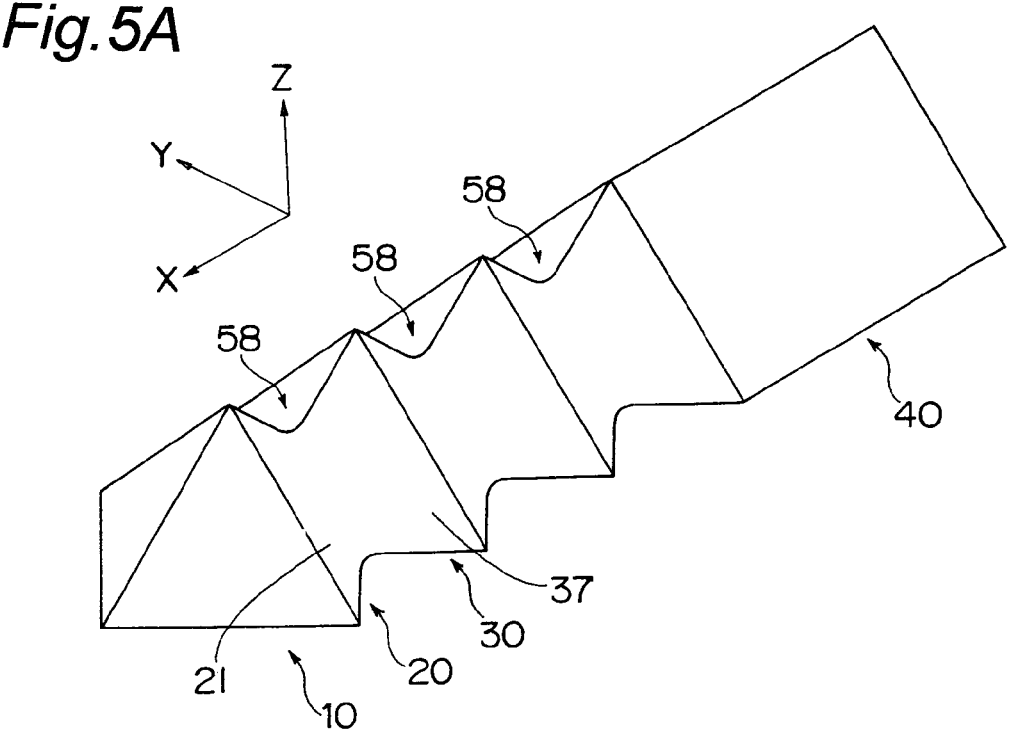
FIGS. 5A-5C are perspective, side, and top plan views of another lancet according to the first embodiment.
Figure 5B:
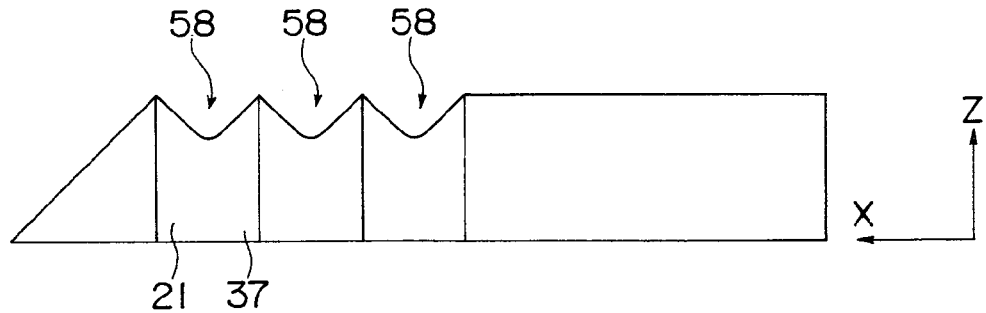
Figure 5C:
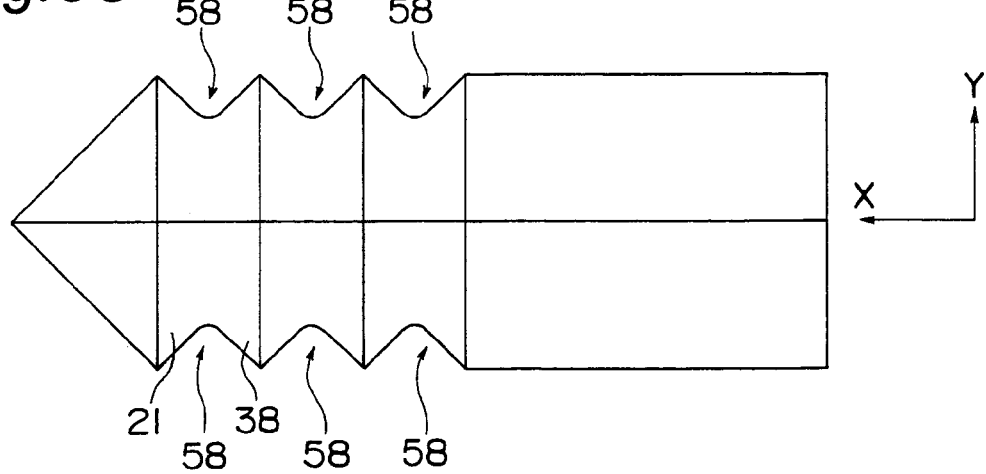

As above, the side surface 21 of the descending region 20 and the side surface 37 of the second ascending region 30 are described as flat planes so that an angled portion (discontinuous portion) is formed therebetween. Contrary, as illustrated in FIG. 5, the lancet 1 may have a continuous curved portion 58 smoothly connecting the side surface 21 of the descending region 20 and the side surface 37 of the second ascending region 30. The continuous curved portion 58 makes the lancet 1 even stiffer against the stress otherwise concentrated on that portion.

Also, it should be noted that although the cross-section of the holding region 40 taken along any Y-Z planes is illustrated to be a triangle, it can be a rectangle or any other shapes for appropriate fit to an external holder mechanism (not shown).

Embodiment 2

With reference to FIGS. 6 to 9, the second embodiment of the lancet according to the present invention will be described herein. The lancet 2 of the second embodiment is similar to the lancet 1 of the first embodiment except that it additionally includes a constant region (reinforcing region). Therefore, the duplicated description in detail for the common features will be eliminated.

Figure 6:
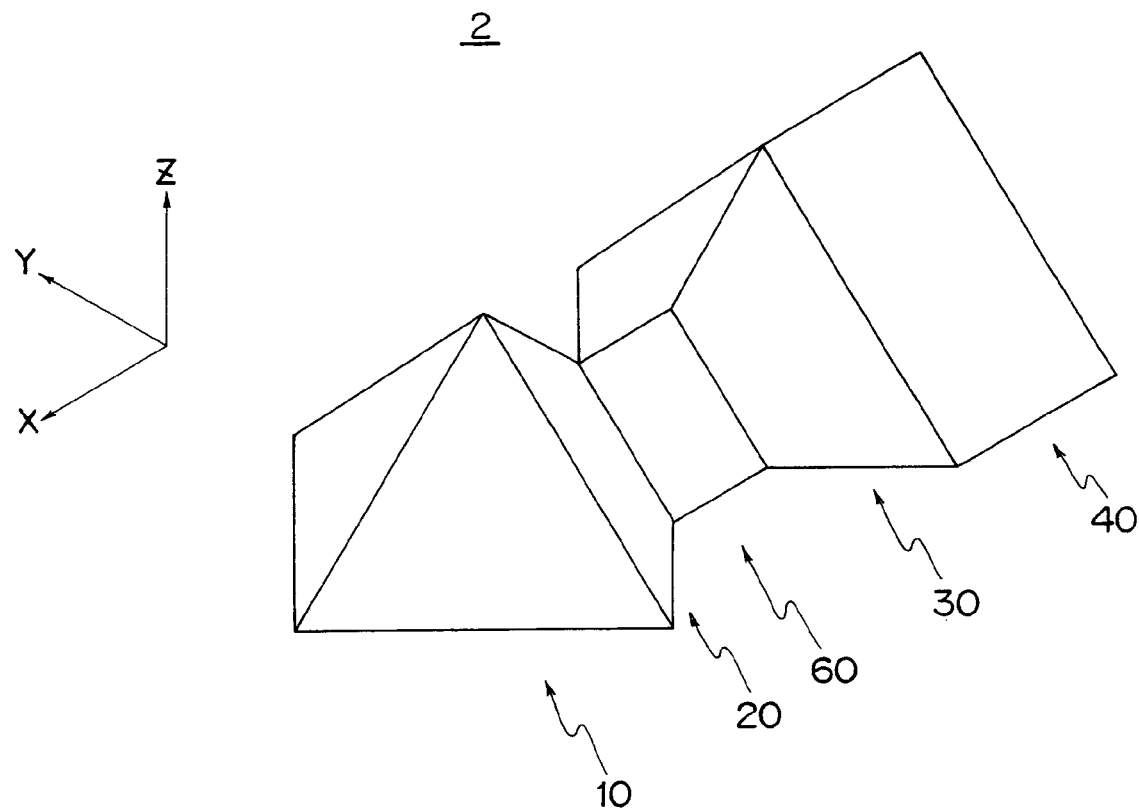
FIG. 6 is a perspective view of a lancet according to the second embodiment of the present invention.
Figure 7A:
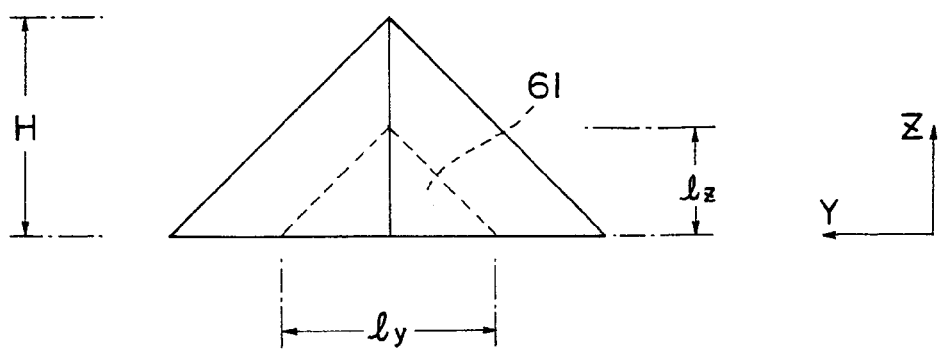
FIGS. 7A-7C are front elevational, side, and top plan views of the lancet shown in FIG. 6, respectively.
Figure 7B:
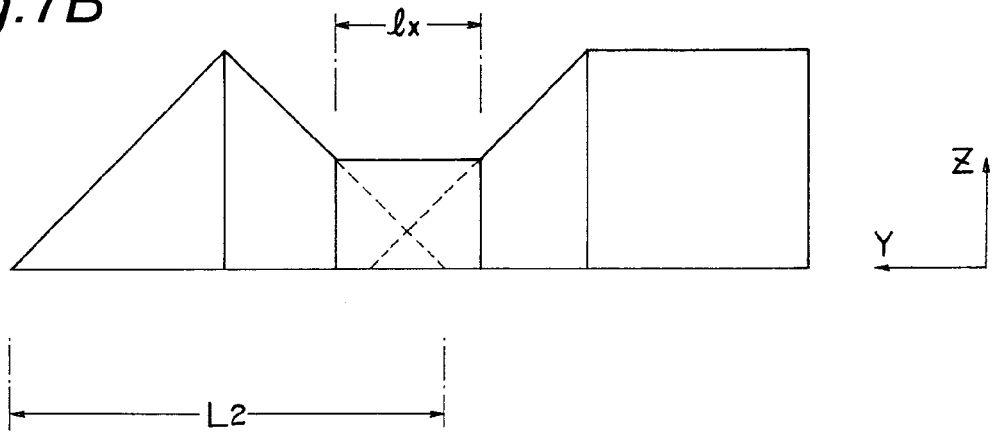
Figure 7C:
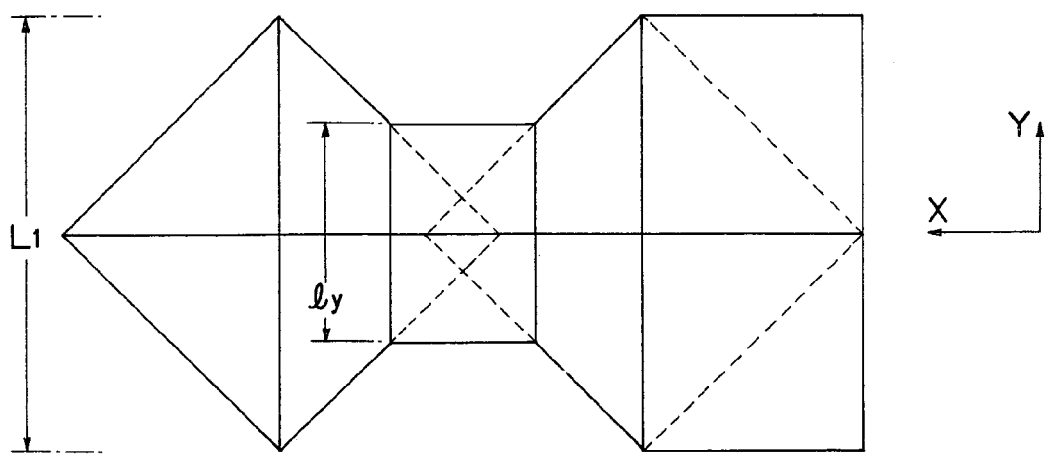

As above, the lancet 2 of the second embodiment has a constant region (reinforcing region) 60 for reinforcing the strength of the lancet 2 between the first descending region 20 and the second ascending region 30 as shown in FIGS. 6 and 7. The constant region 60 has an outer configuration of a triangular prism having a size of X-, Y-, and Z-directions ($l_x$, $l_y$, $l_z$) with a triangular base 61 that is substantially the same shape and size as the smallest cross-section in the descending region 20. Thus, the constant region 60 has a triangle cross-section having a base ($l_y$) and a height ($l_z$) as taken along any Y-Z planes.

According to the second embodiment, similar to the first embodiment, the base and the height ($l_y$, $l_z$) of the constant region 60 are designed to be approximately greater than a half, preferably a two-thirds (⅔) of those of the largest cross-section($L_1$, H), respectively, i.e., $$l_y \geq L_1/2, l_z \geq H/2;\text{ and preferably,}$$

$$l_y \geq 2L_1/3, l_z \geq 2H/3.$$

This design reinforces the strength between the descending region 20 and the second ascending region 30 so as to realize a more stubborn lancet 2.

Figure 8:
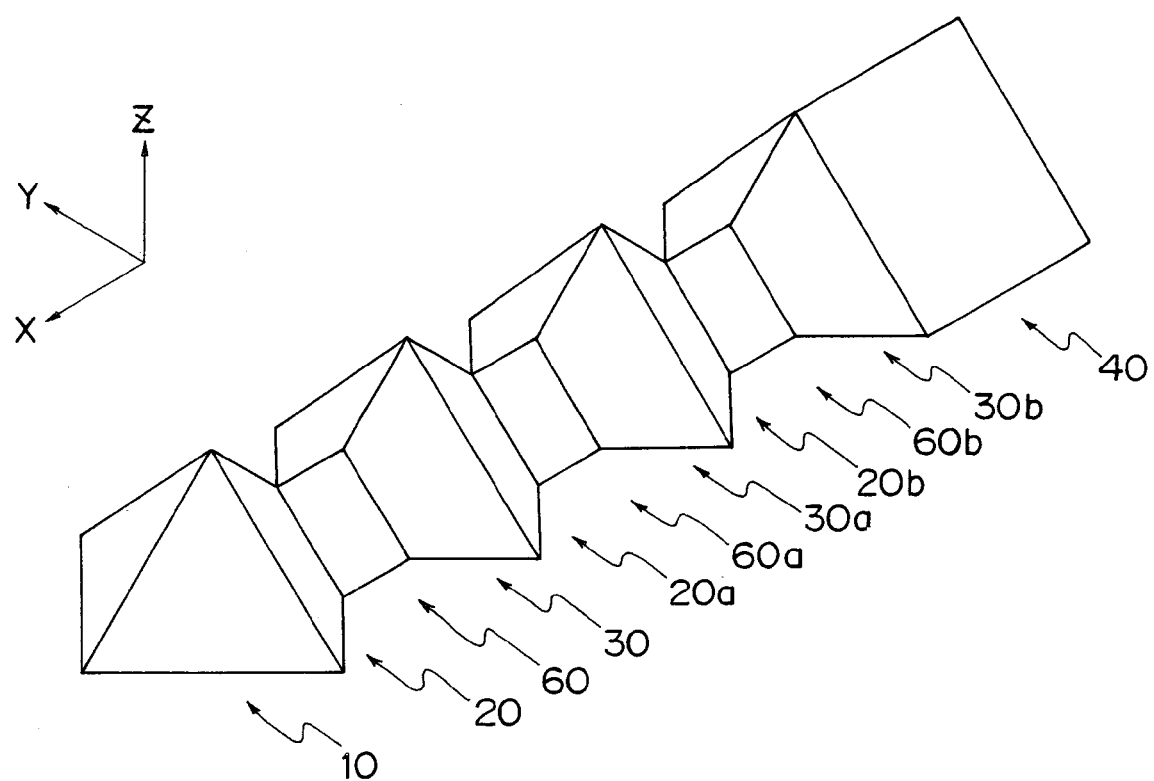
FIG. 8 is a perspective view of another lancet according to the second embodiment.

Also as the first embodiment, the lancet 2 of the second embodiment may include at least one additional descending region 20a, 20b, the constant region 60a, 60b, and the ascending region 30a, 30b, as illustrated in FIGS. 8 and 9.

Embodiment 3

With reference to FIG. 10, the third embodiment of the lancet according to the present invention will be described herein. The lancet 3 of the third embodiment is similar to the lancet 1 of the first embodiment except that the lancet tip is formed sharper than that of the first embodiment. Therefore, the duplicated description in detail for the common features will be eliminated.

Figure 10A:
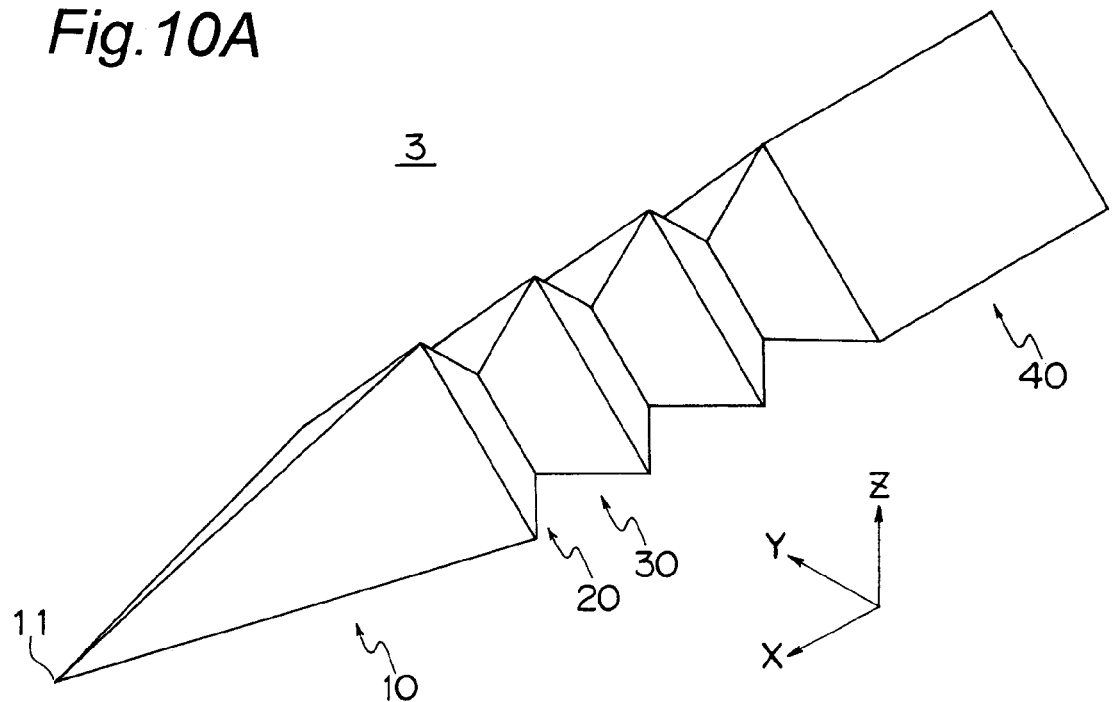
FIGS. 10A-10C are perspective, side, and top plan views of a lancet according to the third embodiment of the present invention.
Figure 10B:
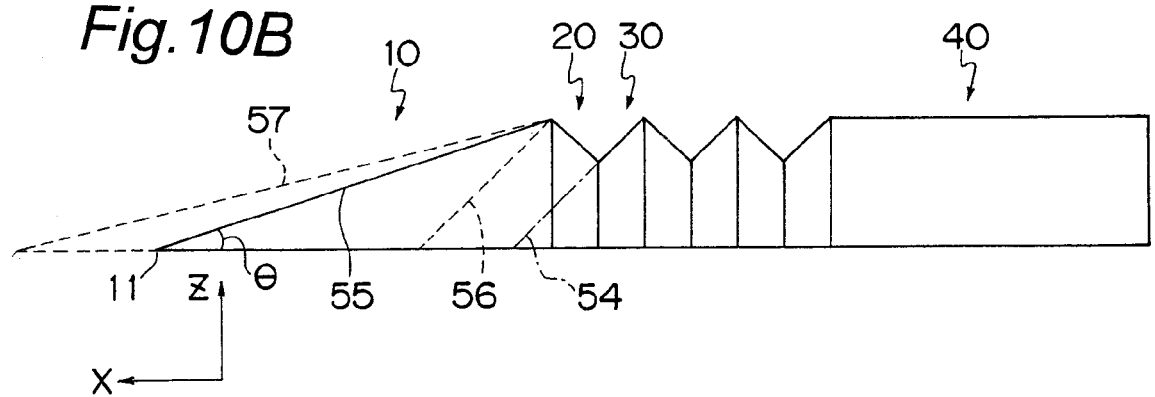
Figure 10C:
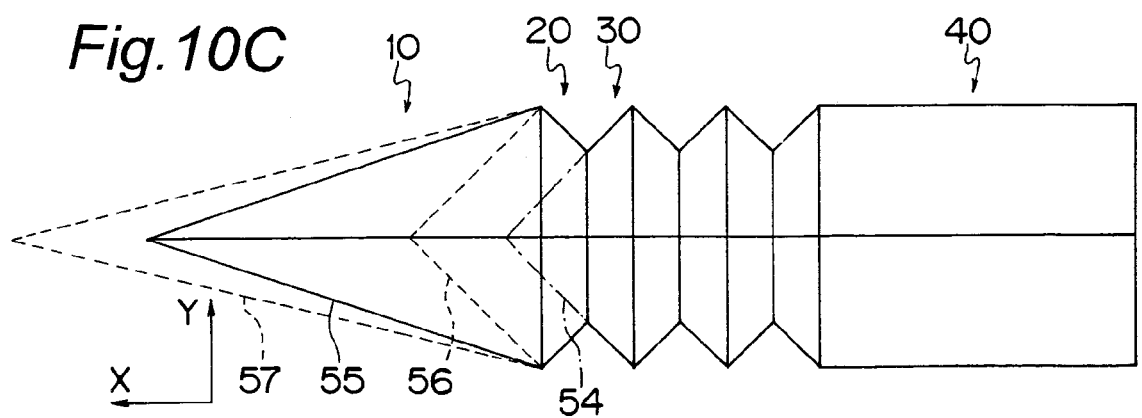

In FIGS. 10B and 10C, the first and second ascending region 10, 30 are designed so as to have the triangular cross-section taken along any Y-Z planes, of which height and base are increased linearly as being away from the tip 11 with gradients (increasing rates) indicated by a solid line 55 and a one-dotted line 54, respectively. Also, the increasing rate (k) of the height and base of the first ascending region 10 indicated by the solid line 55 varies from an increasing rate ($k_1$) indicated by one imaginary line 56 to another increasing rate ($k_2$) indicated by another imaginary line 57, i.e., $$k_2(57) \leq k(55) \leq k_1(56).$$

The imaginary line 56 is parallel to the one-dotted line 54 of the second ascending region 30 having the increasing rate ($k_0$), and the other imaginary line 57 is approximately a quarter of the increasing rate ($k_0$), i.e., $$k_0/4(57) \leq k(55) \leq k_0(56).$$

Preferably, the increasing rate (k) of the height and the base of the first ascending region 10 is set to one-third (⅓) of the increasing rate ($k_0$) of the second ascending region 30, i.e., $$k = k_0/3.$$

Therefore, when the increasing rate of the cross-section (area) of the second ascending region 30 is represented by ($K_0$), the increasing rate (K) of the cross-section (area) of the first ascending region 10 falls within a range between one-sixteenth (1/16; square of a quarter) and one of the second ascending region 30, i.e., $$K_0/16 \leq K \leq K_0.$$

Preferably, the increasing rate (K) of the cross-section of the first ascending region 10 is set to one-ninth (1/9; square of ⅓) of the increasing rate ($K_0$) of the second ascending region 30, i.e., $$K = K_0/9.$$

For example, suppose if the rectangle pyramid defining the outer configuration of the ascending and descending regions includes the first and second diagonals ($L_1$, $L_2$) of the same length and the height that is the same as a half of the diagonals, i.e., $H = L_1/2 = L_2/2$. Then, the first ascending region has the length in the X-direction varying between $L_1/2$ to $2L_1$, preferably $3L_1/2$, and also the tip angle (θ) indicated in FIG. 10B varies between about 14 degree to 45 degrees, preferably is about 18.3 degree.

According to the lancet 3 of the third embodiment, the height and the base of the cross-section in the first ascending region 10 are more moderately increased than those in the second ascending region 30 so that lancet tip 11 of the embodiment is sharper and more elongated. This contributes the lancet 3 of the third embodiment to be penetrated more smoothly into the deep inside with less resistance, thereby further reducing the pain to the patient.

As persons skilled in the art can easily conceives, the lancet of foregoing embodiments can be manufactured, for example, by use of ROBONANO α-0iA® commercially available from FUNAC Ltd. in Yamanashi Pref., JAPAN.

(Modification 1)

With reference to FIGS. 11 to 13, the first modification of the lancet will be described herein. The lancet 101 of the first modification is similar to the lancets 1, 2, 3 of the first to third embodiments except that at least one channel and chamber are provided within the lancet. Therefore, the duplicated description in detail for the common features will be eliminated.

The lancet 101 of the first modification includes at least one channel 71 extending through the incising regions 10, 30 and the releasing region 20 of the lancet 101 as illustrated in FIG. 11A. Preferably, the holding region 40 includes at least one chamber 81 in communication with the channel 71, which has the rectangular cross-section taken along any Y-Z planes as shown in FIG. 11C. Also, the lancet 101 has at least one opening 72 close to the tip 11, extending through any appropriate surfaces such as the bottom surface 73 of the descending region 20.

The lancet 101 having the channel 71 and the chamber 81 can be used in various applications. For example, a pair of electrodes (not shown) spaced away from each other may be arranged within the channel 71 and also a bio-sensor (not shown) such as a Micro Total Analysis System (μ-TAS) may be received in the chamber 81. When the lancet 101 so structured is penetrated into the body, blood plasma drawn through the opening 72 into the channel 71 can instantly and readily be analyzed by the μ-TAS.

Also, the lancet 101 of the first modification can be used as an injection needle. Thus, a micro-pump (not shown) is connected with the chamber 81, and once the lancet 101 is pierced into the body, negative pressure is applied to the chamber 81 so as to easily sample a drop of blood.

Instead of the channel 71 and the opening 72 as shown in FIG. 11, the lancet 101 may include a groove 74 extending along the X-direction on the bottom surface 73 as illustrated in FIG. 12. Also, the lancet 101 may include a pair of electrodes arranged within the groove 74 and also a bio-sensor received in the chamber 81 to analyze the desired component of blood. When the lancet of FIG. 12 is pierced inside the patient's body, the groove 74 in cooperation with the peripheral tissue also defines the capillary tube so that blood plasma is filled sufficiently within the groove 74.

Alternatively, the lancet 101 of the modification may include a plurality of channels extending in the X-direction and a plurality of chambers in the holding region 40, each of channels separately communicating with corresponding one of the chambers (two channels 75, 76 and two chambers 82, 83 are shown in FIG. 13). Also, a plurality of openings 77a-77c, and 78a-78c are formed adjacent the tip 11, for example, extending through the side surfaces of the regions 10, 20, 30 as illustrated in FIGS. 13A and 13B. Each of the channels 75, 76 may receive the independent electrode pairs and also each of the chambers 82, 83 may include a different bio-sensors therein for analyzing a plurality types of blood components.

Further, plural kinds of medicaments may be reserved within the chambers 82, 83 for gradually releasing the medicaments into the patient's body through the openings 77, 78. If desired, each of the openings 77, 78 may be sealed by a sheet (not shown) made of the same biodegradable material so as to allow the medicaments to be gradually released a predetermined time after the lancet 101 is stuck in the tissue of the patient. In addition, the thickness of the sheets may be changed depending upon the channels 75, 76 so that the timing for gradual release of the medicaments can be controlled.

More preferably, the adjacent openings 77, 78 are spaced away from each other by a predetermined gap. One example is where each of the electrodes is assembled to be extruded through the respective one of openings 77, 78, then the distance between the electrodes is defined exactly, allowing the fluid between the electrodes to be analyzed in a more precise manner. Also, another example is where a pair of fiber optics are extruded through the openings 77b and 77c so that beams from each of the fiber optics intersect each other, then the fluid at the intersection of the beam can be inspected more accurately due to the precisely defined geometry.

(Modification 2)

Figure 15A:
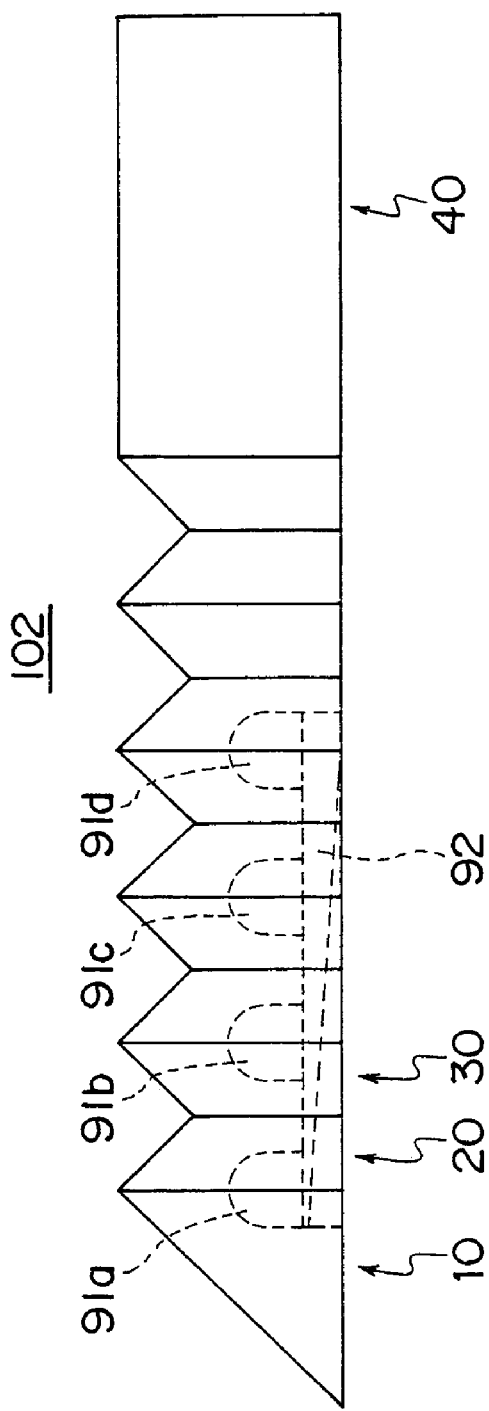
FIGS. 15A and 15B are side views of another lancet of the second modification.
Figure 15B:
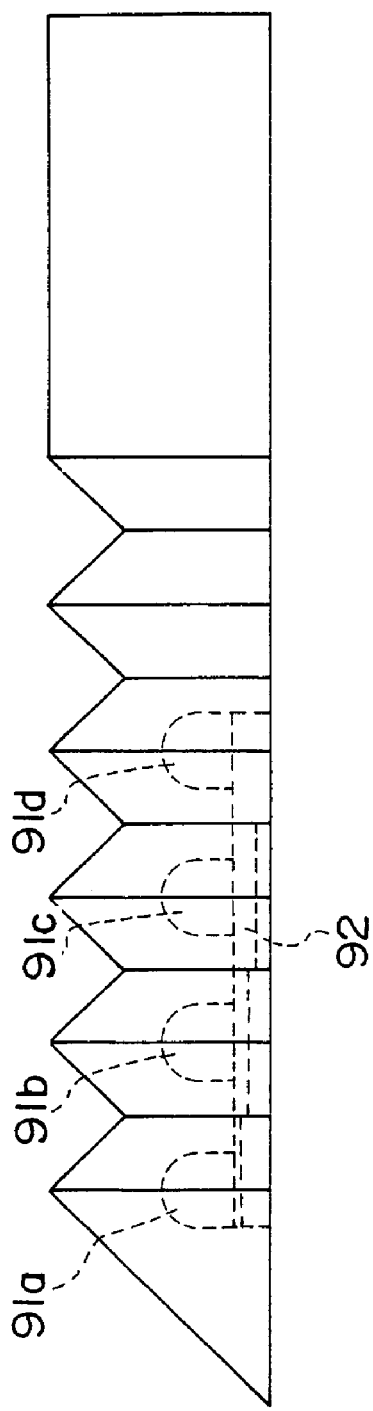

With reference to FIGS. 14 and 15, the second modification of the lancet will be described herein. The lancet 102 of the second modification is similar to the lancets 1, 2, 3 of the first to third embodiments except that a vertical cavity and a seal membrane for sealing the vertical cavity are provided within the lancet. Therefore, the duplicated description in detail for the common features will be eliminated.

As above, the lancet 102 of the second modification includes at least one vertical cavity (four vertical cavities 91a-91d are shown in FIGS. 14A, 14B) extending in a vertical direction (Z-direction) and a seal membrane 92 for sealing the vertical cavity. The vertical cavity 91 receives a micro-particle or fluid containing medicament therein. Also, the seal membrane 92 is made of biodegradable material so that in conjunction with the lancet 102, it seals the vertical cavity to secure the medicament therein without slipping off from the vertical cavity 91.

When the lancet 102 is penetrated and held permanently within the patient body, especially, the biodegradable material especially composing the seal membrane 92 is gently degraded so that medicament contained within the micro-particle or the like received in the vertical cavity 91 is gradually released. Preferably, in case where a plurality of cavities for different medicaments are provided, the seal membrane 92 is designed such that it has the thickness in the Z-direction varying based upon the position of the vertical cavities 91a-91d. In one example shown in FIG. 15A, the seal membrane 92 has the thickness tapered towards the tip 11, and in another example shown in FIG. 15B, the seal membrane 92 is stepped such that it is the thinnest at the cavity 91a, and the second thinnest at the cavity 91b, and the thickest at the last cavity 91d. This structure controls the timing for gradual release of the medicament received in the vertical cavities 91a-91d.

It should be noted that as persons skilled in the art easily conceive and practice, the channel 71, the chamber 81, the openings 77, 78, and the vertical cavities 91a-91d of the first and second modifications are formed with use of a laser device such as an excimer laser emitting laser beam having adjustable power.

Embodiment 4

With reference to FIGS. 16 to 18, the fourth embodiment of the lancet will be described herein. The lancet 4 of the fourth embodiment is similar to the lancet 1 of the first embodiment except that while the latter has the triangular cross-section taken along any Y-Z planes, the former has the trapezoidal cross-section taken along any Y-Z planes. Therefore, the duplicated description in detail for the common features will be eliminated.

Figure 16A:
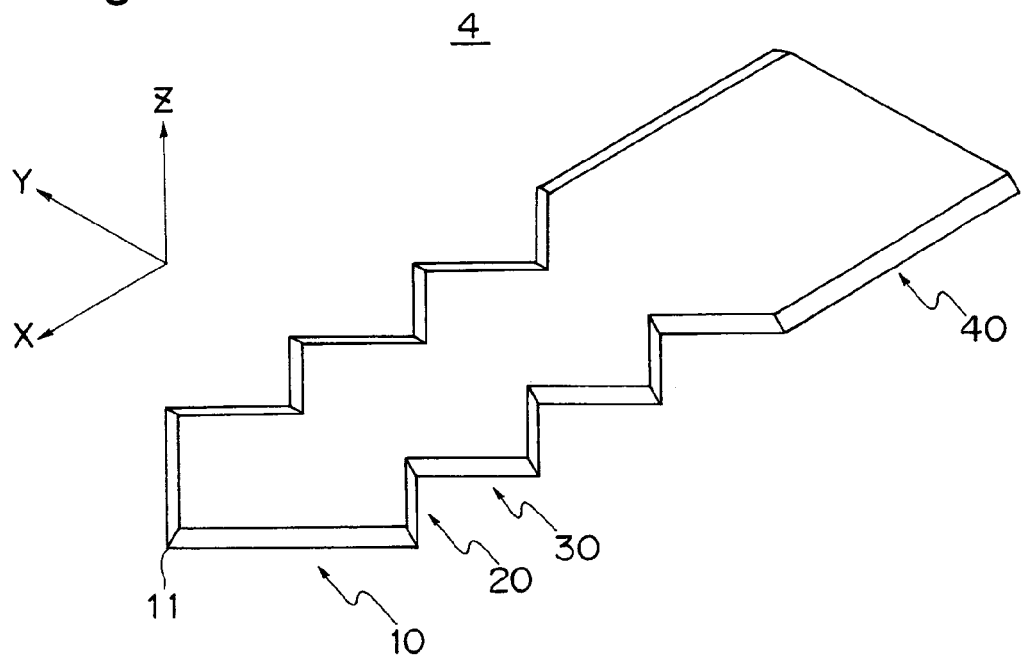
FIGS. 16A and 16B are perspective views of a lancet according to the fourth embodiment of the present invention.
Figure 16B:
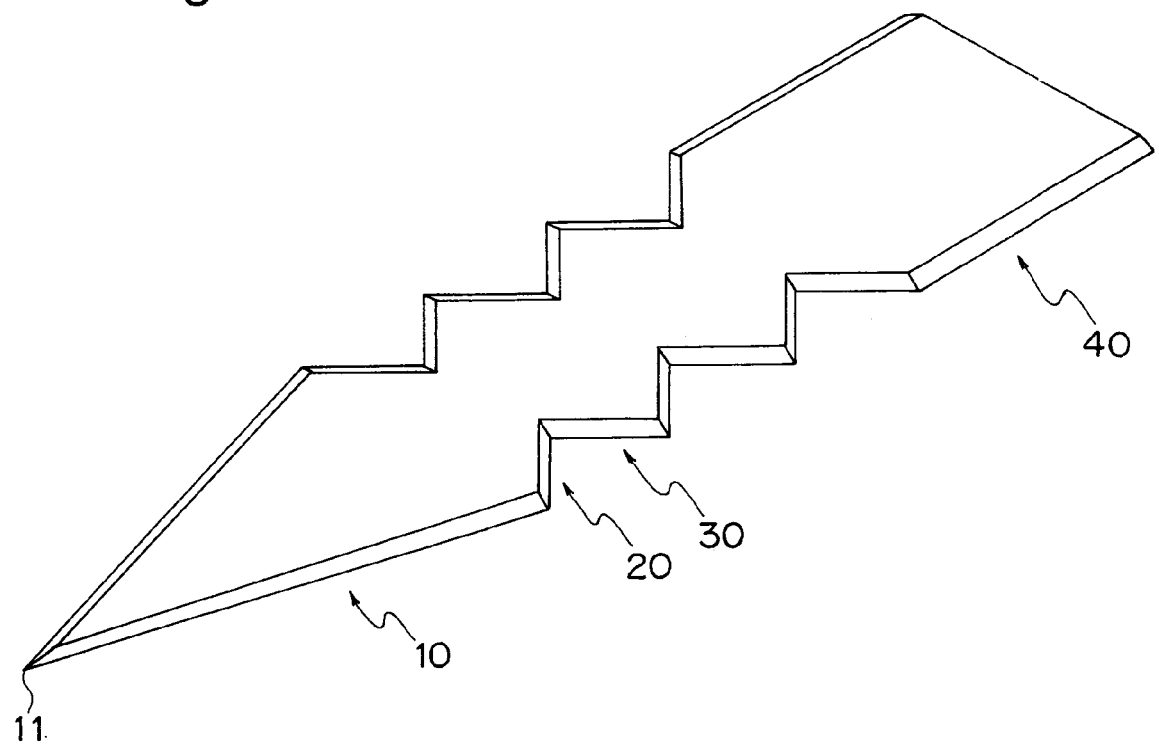

As clearly being understood by comparing FIGS. 3 and 10A of the first embodiment with FIGS. 16A and 16B of the fourth embodiment, respectively, the lancet 4 of the present embodiment has the trapezoidal, rather than triangular, cross-sections taken along any Y-Z planes. The trapezoid has the base (i.e., each of the upper and lower bases) varying in accordance with the distance from the lancet tip 11 or the position in the X-direction, and the height (H) that is constant. Thus, the lancet 4 of the present embodiment includes first and second ascending regions (first and second tissue incising regions) 10, 30, of which trapezoidal cross-sections taken along any Y-Z planes has the base monotonically increasing as being away from the tip 11, and a first descending region (first friction releasing region) 20 of which trapezoidal cross-sections taken along any Y-Z planes has the base monotonically decreasing as being away from the tip 11. Also, the holding region 40 is connected with the subsequent ascending region. The lancet 4 of the present invention is integrally made of the aforementioned biocompatible material, or more preferably, made of the biodegradable material so that it can readily be disposed and also retained in the patient's body.

According to the fourth embodiment, the largest trapezoidal cross-section of the first and second ascending regions 10, 30 have bases of substantially the same length. Also, although in view of incising the peripheral cells or tissue, the height (H) of the trapezoidal cross-section is preferably short (the lancet 4 is thin), the height (H) has to be taller than a predetermined dimension for ensuring sufficient strength of the lancet 4. In particular, the lancet 4 of the embodiment preferably has the thickness (H) greater than about one-eighth of the base of the largest cross-section, i.e., the first diagonal ($L_1$) of the rectangular pyramid (i.e., $H \leq L_1/8$).

In FIGS. 17A-17C and 18A-18C, the base of the smallest cross-section is preferably greater than a half, and more preferably greater than about two-thirds of the largest cross-section. Also, like the first embodiment, the largest cross-sections in first and second ascending regions 10, 30 adjacent to each other is spaced away preferably by a predetermined gap (D) of at least 1 micron.

Further, similar to the first embodiment, the lancet 4 of the fourth embodiment may include at least one additional descending region and ascending region integrally formed with the second ascending region 20. Also, similar to the second embodiment, the lancet 4 of the fourth embodiment may include at least one additional constant (reinforcing) region having the cross-section of substantially the constant area, which is formed between the descending and ascending regions.

In addition, similar to the third embodiment, the first ascending region 10 of the lancet 4 is designed sharper such that the base of the trapezoidal cross-section increases gently. The increasing rate of the base of the trapezoidal cross-section in the first ascending region 10 falls within a range between about one-fourth and one of the increasing rate of the trapezoidal cross-section in the second ascending region 30. Thus, the lancet 4 of the fourth embodiment is sharp so that it can easily be penetrated into the tissue, minimizing the pain to the patient.

Embodiment 5

With reference to FIGS. 19 and 20, the fifth embodiment of the lancet will be described herein. FIG. 19A is a perspective view of the lancet 5 similar to FIG. 3 (lancet 1) and FIG. 10A (lancet 3). FIG. 19B-19D are front elevational, side, and top plan views of the lancet 5 similar to FIGS. 4A-4C (lancet 1). The lancet 5 of the fifth embodiment is similar to the lancet 1 of the first embodiment except that while the latter has the triangular cross-section taken along any Y-Z planes, the former has a semi-circle cross-section taken along any Y-Z planes. Therefore, the duplicated description in detail for the common features will be eliminated.

The lancet 5 of the present invention extends along the predetermined direction (X-direction) and includes cross-sections taken along a plane (Y-Z plane) perpendicular to the predetermined direction (referred to as a "vertical cross-section" herein), of which cross-sectional area regularly varies based upon the distance from the needle tip 11. Also, the lancet 5 includes a plurality of maximal points 22a-22c where the cross-sectional area is locally maximal, and a plurality of minimal points 23a-23c where the cross-sectional area is locally minimal. In FIGS. 19A-19D, three of the maximal and minimal points are illustrated, any plural number of the maximal and minimal points may be provided.

According to the fifth embodiment, the lancet 5 is designed such that the vertical cross-section at the maximal point 22a closest to the needle tip 11 has the same cross-sectional area as those at any other maximal points 22b, 22c, and the vertical cross-section at the minimal point 23a closest to the needle tip 11 has the same cross-sectional area as those at any other minimal points 23b, 23c. Also, in the lancet 5 shown in FIGS. 19A-19D, a distance (D) between a pair of the adjacent maximal points, e.g., 22a and 22b, is substantially equal to one between another pair of the adjacent maximal points e.g., 22b and 22c.

Further, when the lancet 5 is viewed on a projected plane, i.e., the X-Z plane shown in FIG. 19C and the X-Y plane shown in FIG. 19D, the cross-sectional area of the vertical cross-section varies in a linear manner between one of maximal points and the adjacent one of the minimal points, e.g., between 22a-23a and 23a-22b. In addition, as described for the first embodiment, the cross-sectional area of the vertical cross-section may also vary in a curved manner between one of maximal points and the adjacent one of the minimal points.

When the lancet 5 so structured is penetrated inside the tissue (skin or flesh) of the patient's body, as illustrated in FIG. 19C, it wedges away the peripheral cells around the tip 11 of the first ascending region (first tissue incising region) 10. Since the frictional force between the first ascending region 10 and the peripheral tissue is more significant, as the lancet 5 advances into the tissue, the peripheral tissue may be drawn into the deep inside by the frictional force.

However, according to the fifth embodiment, as the lancet 5 further advances after the first ascending region 10 sinks within the tissue, since the cross-sectional area of the first descending region (first friction releasing region) 20 is decreased, thus, the frictional force between the lance 5 and the peripheral tissue is reduced. This allows the peripheral cells to return to the normal position due to its elasticity. To this end, the peripheral cells drawn by the first ascending region 10 is returned to the original position and released from the physical stress applied thereto.

Then, as the second ascending region 30 advances into the tissue, it also wedges away the peripheral cells for penetration. As above, the vertical cross-section at the maximal point 22a closest to the needle tip 11 is designed to have the same cross-sectional area as those at any other maximal points 22b, 22c, the peripheral tissue can avoid suffering from being stretched (stressed) beyond the degree as required for penetration by the descending regions such as second ascending region 30.

Figure 20A:
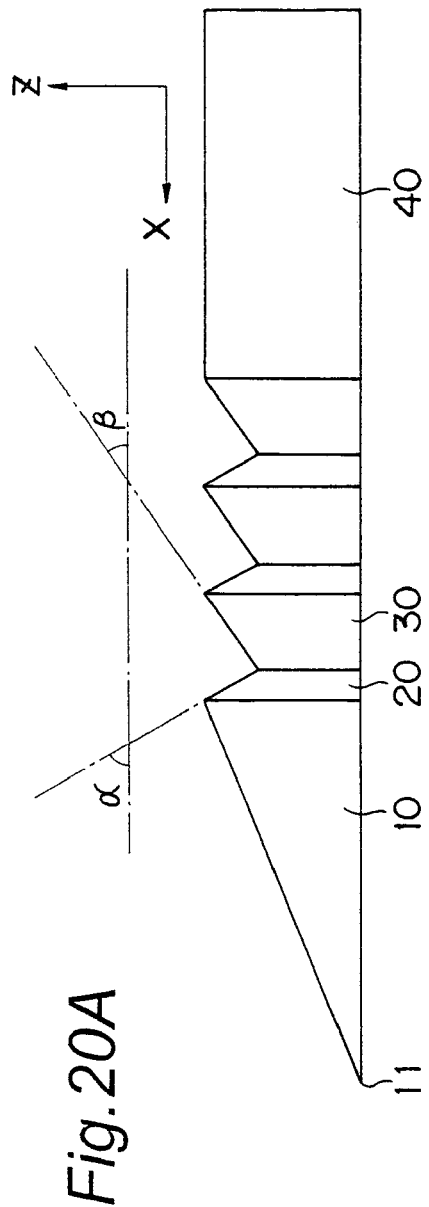
FIG. 20A-20B are side and top plan views of the another lancet of the fifth embodiment.
Figure 20B:
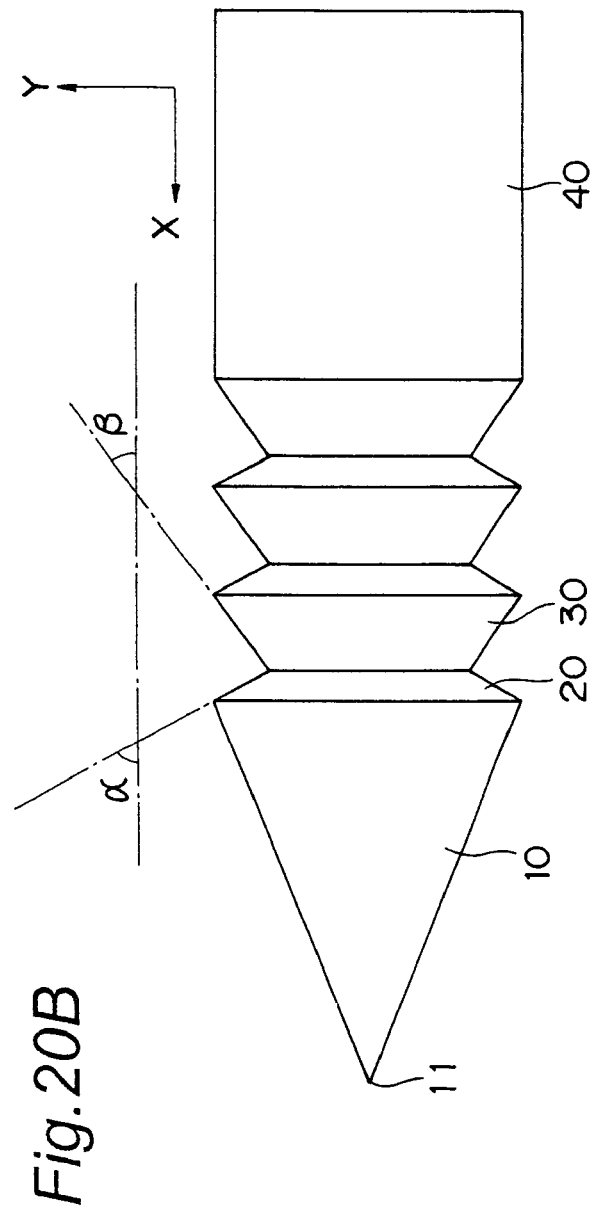
Figure 22A:
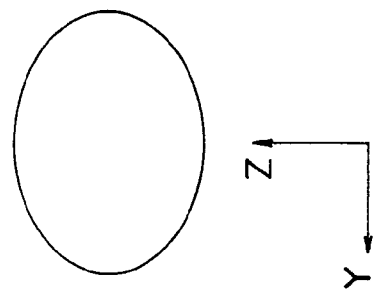
FIGS. 22A-22C are front elevational, side, and top plan views of the lancet according to the fourth modification of the fifth embodiment.
Figure 22B:
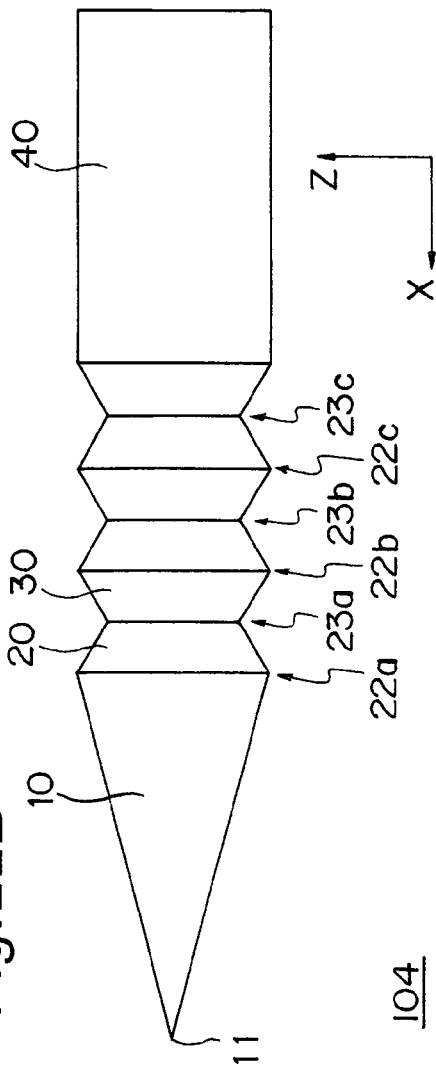
Figure 22C:
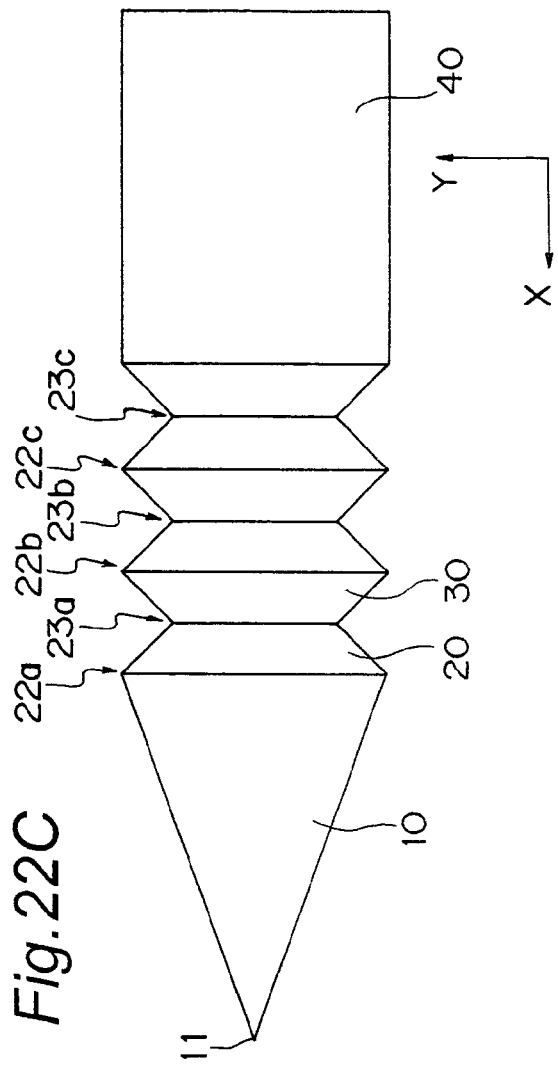
Figure 24A:
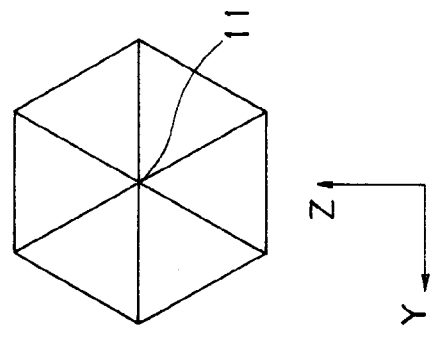
FIGS. 24A-24C are front elevational, side, and top plan views of the lancet according to the sixth modification of the fifth embodiment.
Figure 24B:
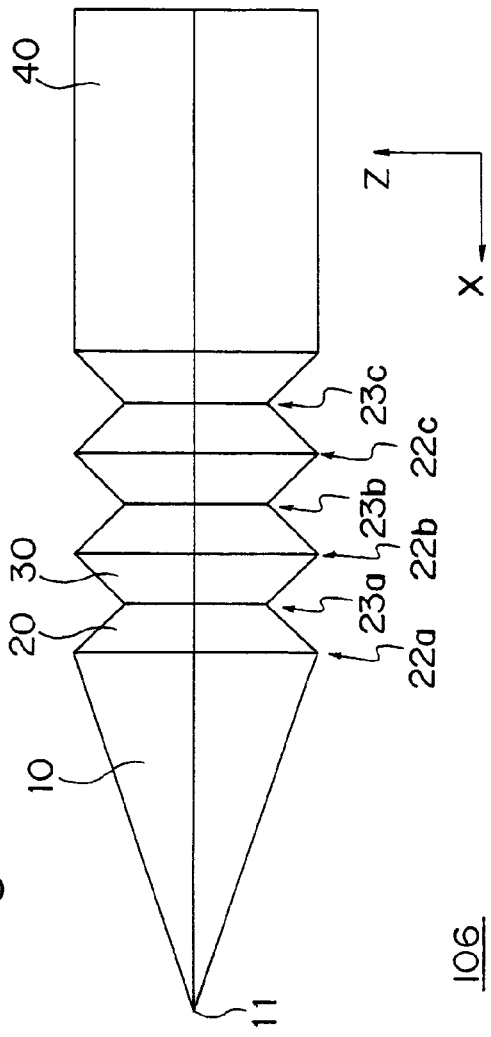
Figure 24C:
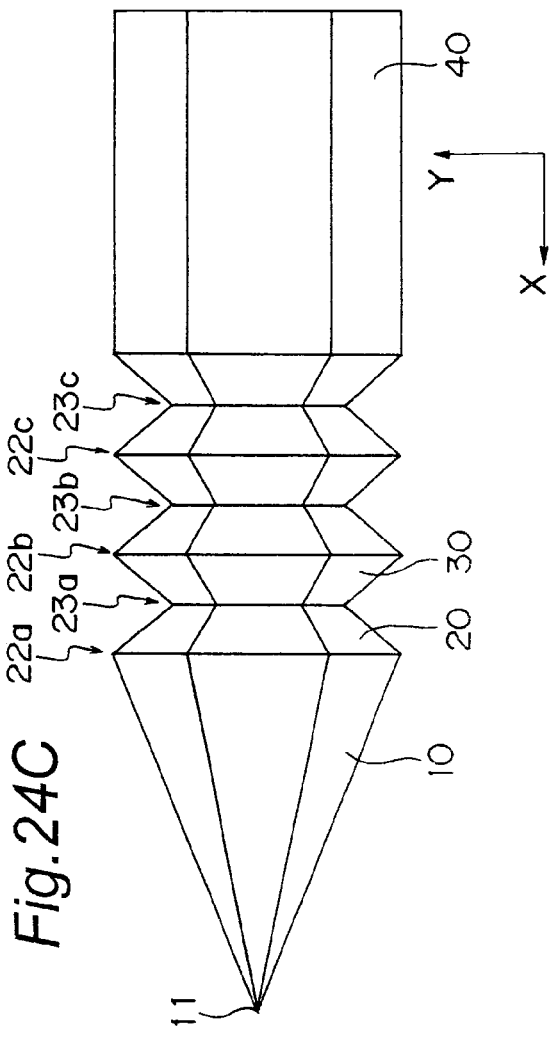

Preferably, when the lancet 5 is viewed on projected planes, i.e., the X-Z plane shown in FIG. 20A and the X-Y plane shown in FIG. 20B, the angle (a) between the X-axis and the side surface of the descending region 20 is greater than the angle (β) between the X-axis and the side surface of the ascending region 30. This leads rapid reduction of the cross-sectional area in the second descending region 20 when the lancet 5 of the present invention is penetrated beyond the first ascending region 10, so that the frictional force between the tissue and the lancet 5 is reduced in a quicker manner for facilitating the peripheral tissue to return to the original position.

As above, according to the present invention, the present invention provides a non-invasive lancet 5 reducing the pain to the patient by returning the peripheral cells across the substantial area back to the original position and by minimizing the damage of the peripheral cells.

(Modifications 3-6)

Referring to FIGS. 21 to 24, the third to sixth modifications of the lancet 5 according to the fifth embodiment will be described herein. The lancet 5 of the fifth embodiment has the vertical cross-section of a semi-circle configuration taken along any Y-Z planes. Meanwhile, the lancets 103, 104, 105, 106 of the third to sixth modifications are similar to the lancet 5 of the fifth embodiment except that they have the vertical cross-sections of a circle, oval, rectangular, hexagonal configurations, as illustrated in FIGS. 21A-21C, 22A-22C, 23A-23C, and 24A-24C, respectively.

Therefore, the lancets 103, 104, 105, 106 of the third to sixth modifications has the same advantage as the lancet 5 of the fifth embodiment, i.e., substantially reducing the pain of the patient and minimizing the unrecoverable damage to the peripheral cells across a substantial area.

Embodiment 6

Figure 25:
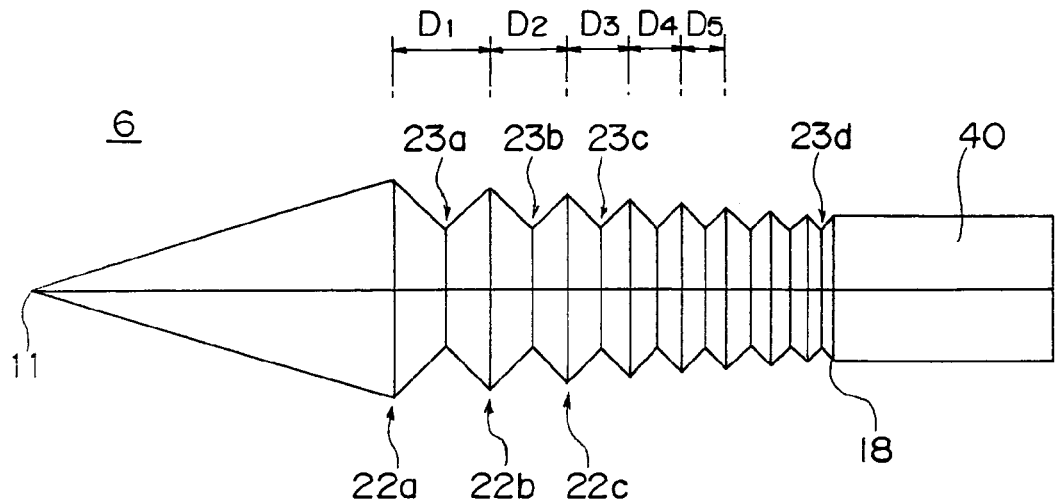
FIG. 25 is a top view of the lancet according to the sixth embodiment.

Referring to FIG. 25, the sixth embodiment of the lancet will be described herein. FIG. 25 is a top plane view of the lancet 6 similar to FIG. 4C (lancet 1) and FIG. 10C (lancet 3). According to the lancet 1 of the first embodiment, the vertical cross-sections at the maximal points have the same cross-sectional area as each other. Contrary, in the lancet 6 of the sixth embodiment, the vertical cross-section at the maximal point 22a closest to the needle tip 11 has the cross-sectional area greater than those at other maximal points 22b, 22c, in particular, the cross-sectional area of the vertical cross-sections at the maximal points are smaller as the vertical cross-section is closer to the lancet rear 18. Besides that, since the lancet 6 of the sixth embodiment has a structure similar to that of the lancet 1, the duplicated description in detail for the common features will be eliminated.

Also, as clearly illustrated in FIG. 25, the distances (D1-D5) between a pair of the adjacent maximal points 22a-22c of the lancet 6 are shorter as closer to the lancet rear 18. Meantime, the cross-sectional area of the vertical cross-sections at the minimal points 23a-23d are constant.

In general, when the lancet 6 is pierced into the body, i.e., when the lancet tip 11 is in the tissue and the holing member 40 is supported by a user, a significant stress is likely concentrated on the lancet rear 18, and lancet 6 may be broken off at the minimal point 23d adjacent to the lancet rear 18.

However, according to the sixth embodiment of the present invention, since the lancet 6 is designed such that the cross-sectional area at each of the minimal points 23a-23d is constant, it can be stiff at the minimal point 23d adjacent to the lancet rear 18 to realize a safer lancet 6.

(Modification 7)

Figure 26:
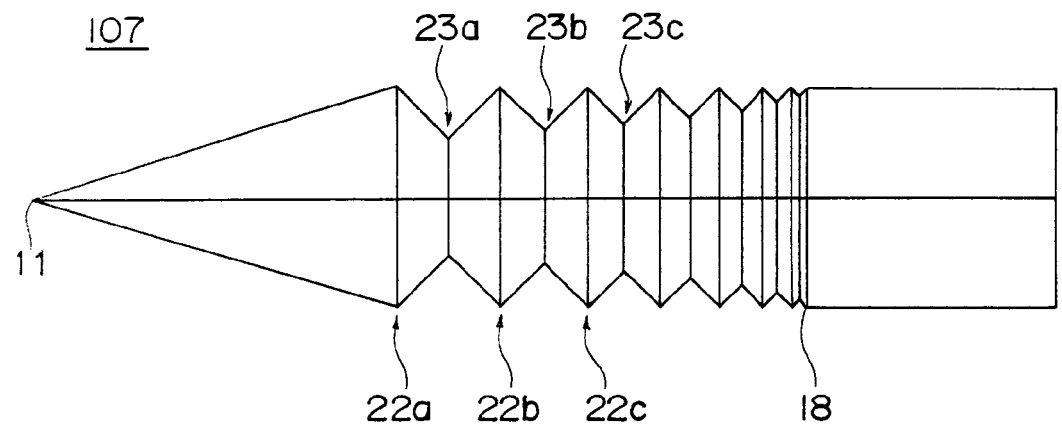
FIG. 26 is a top view of the lancet according to the seventh modification of the sixth embodiment.

Referring to FIG. 26, the seventh modification of the sixth embodiment will be described herein. The lancet 107 of the seventh modification is designed such that while the cross-sectional area of the vertical cross-sections at the maximal points 22a-22c are constant, the cross-sectional area of the vertical cross-sections at the maximal points 23a-23d are smaller as the vertical cross-section is closer from the tip 11 to rear 18 (in the reverse direction of the X-axis). Thus, the vertical cross-section 23d has the cross-sectional area greater than those at the other vertical cross-sections 23a-23c. Therefore, according to the seventh modification, the lancet 107 can be stiffer at the minimal point 23d adjacent to the lancet rear 18 and safer than the lancet of the sixth embodiment.

(Modification 8)

Figure 27:
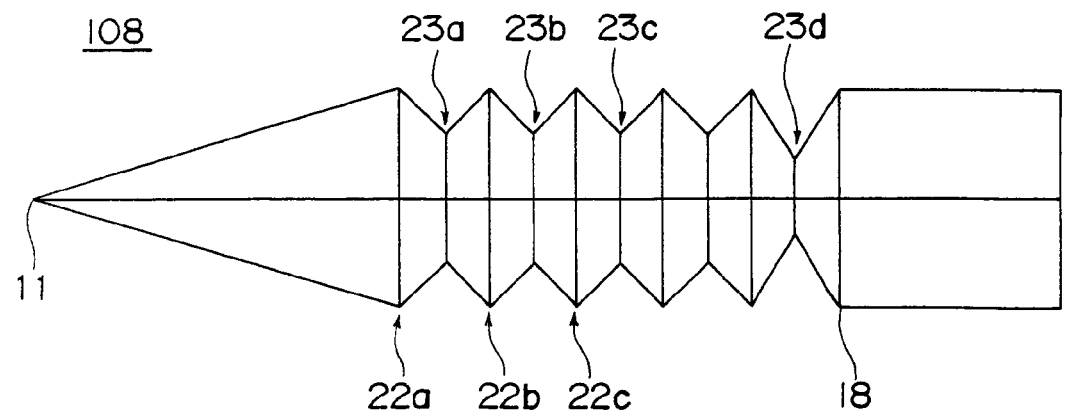
FIG. 27 is a top view of the lancet according to the eighth modification of the sixth embodiment.

Referring to FIG. 27, the eighth modification of the sixth embodiment will be described herein. In the lancet 108 of the eighth modification, the cross-sectional area of the vertical cross-sections at the maximal points 22a-22c are constant, and the cross-sectional area of the vertical cross-sections at the minimal points 23a-23c except 23d are constant. Thus, the cross-sectional area only at the minimal point 23d closest to the lancet rear 18 is smaller than those at the other minimal points 23a-23c.

In the lancet 108 so structured, after it is pierced into the tissue, it may be intentionally broken off at the minimal point closest to the lancet rear 18 to allow the broken portion of the lancet 108 being remained within the tissue. In case where the lancet 108 is used to be remained in the tissue, it should be formed of the biodegradable material such as polylactide.

In addition, the lancet 107 and 108 has the same advantage as the lancet 6, substantially reducing the pain of the patient and minimizing the unrecoverable damage to the peripheral cells.

(Modification 9)

Figure 28A:
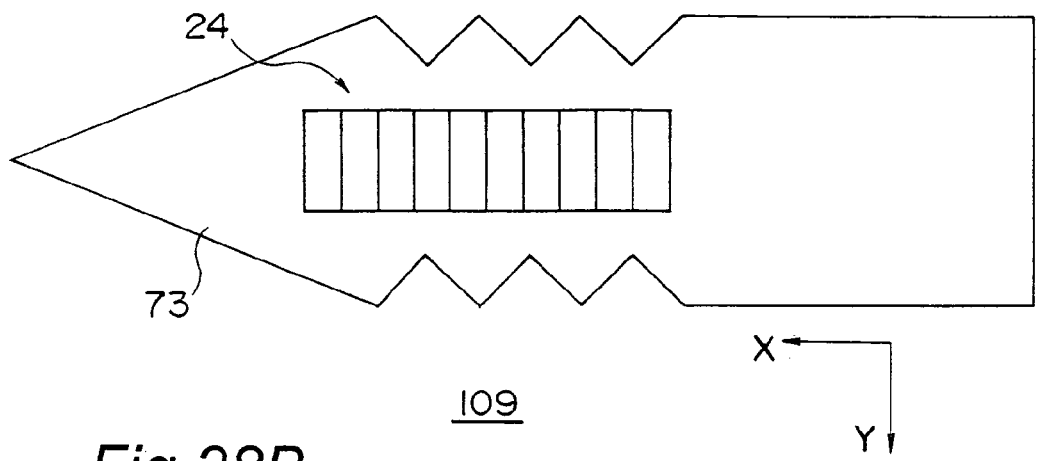
FIGS. 28A-28C are bottom, cross-sectional, enlarged views of the lancet according to the ninth modification of the above embodiments, showing a grating.
Figure 28B:
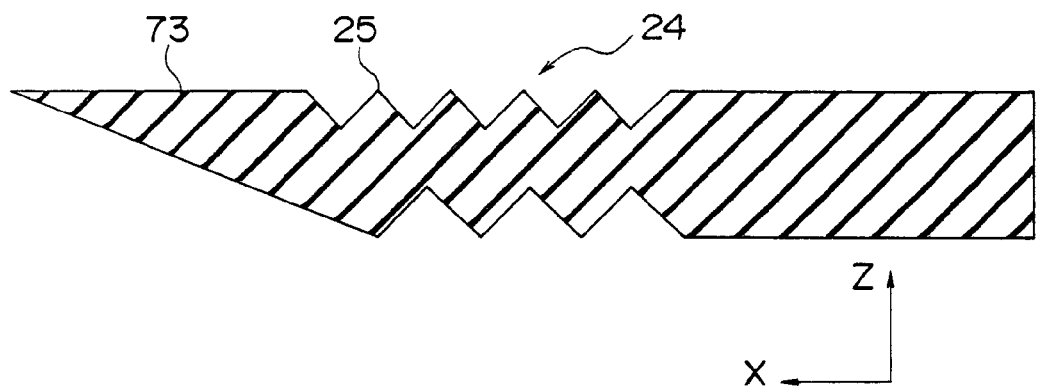

Referring to FIG. 28, the ninth modification of the above-described embodiments will be described herein. FIG. 28A is a bottom plane view of the lancet 109 of the ninth modification when viewed from the bottom to the top (in the Z-direction), and FIG. 28B is a cross-sectional view taken along the X-Z plane. The lancet 109 includes a grating 24 formed on the bottom surface 73.

Figure 28C:
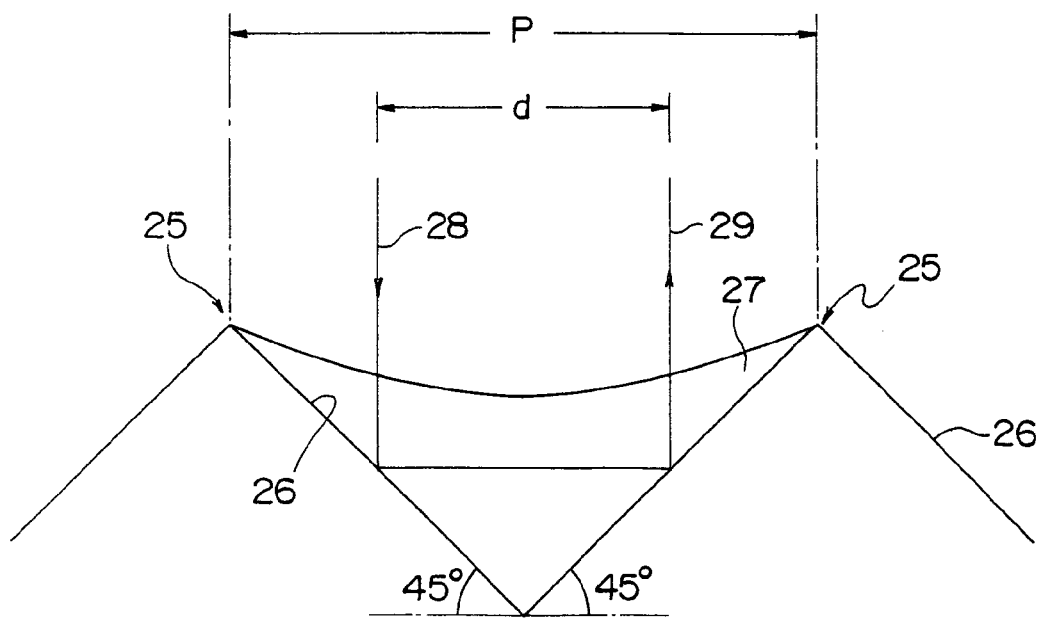

As illustrated in the enlarged view of FIG. 28C, the grating 24 has a distance (pitch) (P) between a pair of adjacent peaks 25, and inclined surfaces 26 e.g., at 45 degrees with the X-axis.

As the lancet 109 is pierced into the patient's tissue, blood 27 is adhered on the inclined surfaces 26. The interface between blood 27 and atmosphere follows the curved trace as shown in FIG. 28C, which may vary depending upon surface tension between blood in a liquid form and material of the inclined surfaces 26. For example, the grating 24 is made of polylactide of higher hydrophilicity, more amount of blood is adhered on the grating 24. An incident beam 28 irradiated by a laser radiator (not shown) from the above reflects at the inclined surfaces 26 twice, and the reflected beam 29 returns to a laser detector (not shown). Suppose that the distance between the incident beam 28 and the reflected beam 29 is represented as (d), the laser beam path is uniquely defined by the distance (d) Thus, the laser beam transmits into blood by the distance (d), causing the phase shift of the laser beam to be detected. Measurement of such phase shift finds the content of keton body and blood sugar in blood. When the particulate body such as erythrocyte is adhered on the grating 24, the measurement of blood sugar may include error. Therefore, the pitch (P) is preferably shorter than the size of the erythrocyte to avoid the adhesion thereof, for example, in the range between 1 to 25 μm.

As described above, according to the lancet 109 of the ninth modification, the laser measurement device (not shown) is used to instantly measure the content of the keton body and blood sugar in blood.

(Modification 10)

Referring to FIG. 29, the tenth modification of the above-described embodiments will be described herein. The lancets 110 illustrated in FIGS. 29A and 29B, which are top plane views similar to FIGS. 4C and 10C, includes the lancet tips 11 having the curvature radius of 10 μm and 3 μm, respectively.

In general, in case where the tip 11 of a lancet or injection needle is round and not sharp, it gives more pain as it is penetrated within the tissue. Thus, it is well-known by those skilled in the art that the sharper tip gives the less pain. However, the dedicated study of the present inventors has revealed that if the lancet 110 with the tip 11 having the curvature radius of approximately 10 μm or less is pierced into the skin, the pain can be substantially reduced.

For that reason, the lancet 110 of the tenth modification is designed such that it includes the tip 11 having the curvature of the radius ($R_1$) of approximately 10 μm or less as shown in FIG. 29A, and preferably having the curvature of the radius ($R_2$) of approximately 3 μm or less as shown in FIG. 29B. To this end, the lancet 110 can be realized to gives less pain to the patient.

Also, the lancet 110 of the tenth modification is designed such that it includes a lot of the maximal and minimal points 22, 23 and the distance between a pair of the adjacent maximal points and a pair of the adjacent minimal points are constant (e.g., D=1 to 25 μm). The lancet so formed can be used as a sort of a dimension gauge when it is pierced within the tissue. Alternatively, it may be marked or colored at the position away from the tip 11 by a predetermined distance to clearly indicate the distance from the tip 11.

(Modifications 11-12)

Figure 30B:
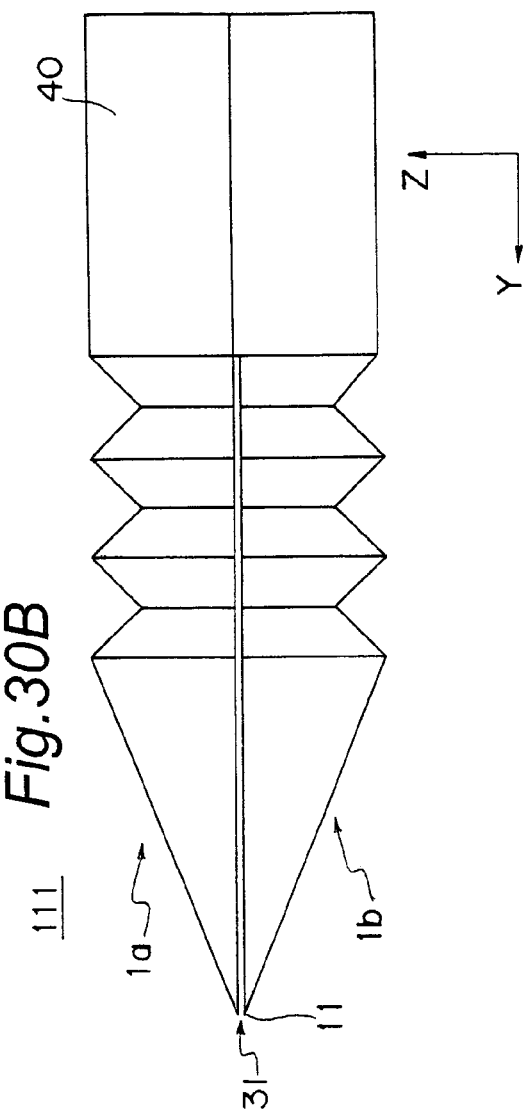
FIGS. 30A-30C are front elevational, side, and top plan views of the lancet according to the eleventh modification of the above embodiments.
Figure 30C:
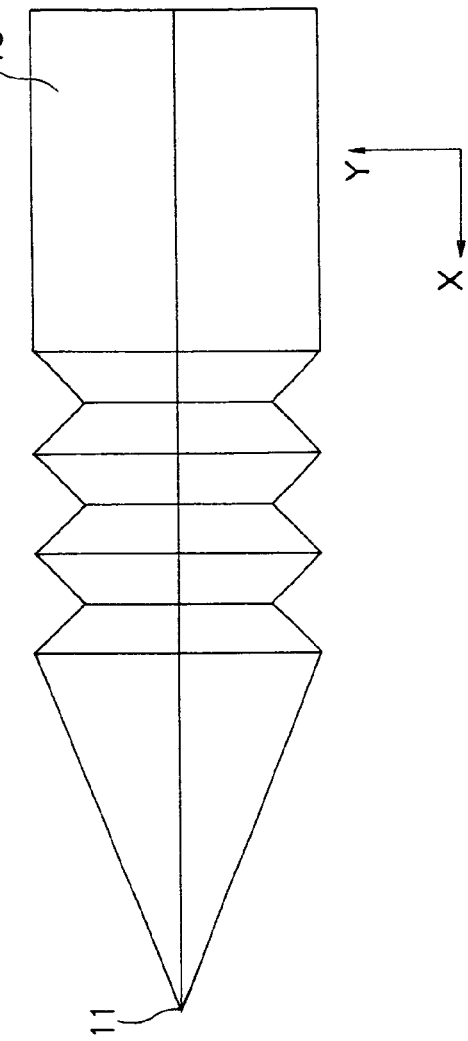
Figure 30A:
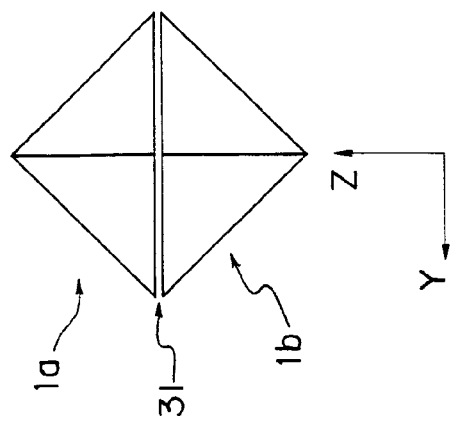

Referring to FIGS. 30 and 31, the eleventh and twelfth modifications of the fifth embodiment will be described herein. FIGS. 30A-30C are front elevational, side, and top plan views of the lancet 111 similar to FIGS. 4A-4C. The lancet 111 of the eleventh modification is formed by combining a pair of lancets 1 of FIGS. 4A-4C with the holding members being secured to each other, and includes a slit 31 between the pair of the lancets 1a, 1b. Also, FIGS. 31A-31C are front elevational, side, and top plan views of the lancet 112 similar to FIGS. 19B-19D. The lancet 112 of the twelfth modification is formed by combining a pair of lancets 5 of FIGS. 19B-19D with the holding members being secured to each other, and includes a slit 31 between the pair of the lancets 5a, 5b.

Therefore, the lancets of the eleventh and twelfth modifications have the same advantage as the lancets 1, 5.

In addition, according to the lancets 111, 112 of the eleventh and twelfth modifications, blood or lymph is drawn through the narrow slit 31 towards the holing member 40 by capillary force. To this result, blood plasma, cells, and proteins contained in blood can easily be sampled.

Although each of the maximal and minimal points, members, and the tips are illustrated as being discontinuous surfaces in the drawings of the above-described embodiments and modifications, as understood by those skilled in the art, each of them may be configured to have smooth curved surfaces, like the continuous surface 58 of FIG. 5.

Therefore, the embodiments and modifications as described above should be understood to merely be illustrative and not limitative for the present invention, which is defined solely by the claims attached herein.

The invention claimed is:

1. A medical needle extending along a predetermined direction and having a vertical cross-section taken along a plane perpendicular to the predetermined direction of which cross-sectional area varies based upon a distance from a needle tip, the medical needle, comprising:
  a plurality of maximal points where the cross-sectional area of the vertical cross-section is locally maximal; and
  a plurality of minimal points where the cross-sectional area of the vertical cross-section is locally minimal;
  wherein the vertical cross-section at the maximal point closest to the needle tip has the cross-sectional area not less than those at any other maximal points, and
  wherein the vertical cross-section between the needle tip and the maximal point closest to the needle tip is gradually and continuously increased in accordance with the distance from a needle tip.

2. The medical needle according to claim 1, further comprising:
  at least one channel formed therein extending along the predetermined direction and having at least one opening.

3. The medical needle according to claim 2, further comprising:
  a holding member connected to a needle rear;
  wherein the holding member has at least one chamber in communication with the channel.

4. The medical needle according to claim 1, further comprising:
  at least one groove extending along the predetermined direction.

5. The medical needle according to claim 4, further comprising:
  a holding member connected to a needle rear;
  wherein the holding member has at least one chamber in communication with the groove.

6. The medical needle according to claim 1,
  wherein when viewed on a projected plane parallel to the predetermined direction, the cross-sectional area varies in a linear manner between one of maximal points and the adjacent one of the minimal points.

7. The medical needle according to claim 1,
  wherein the vertical cross-section has a shape selected from a group consisting of triangle, quadrangle, hexagon, polygon, semi-circle, circle, ellipse, and trapezoidal.

8. The medical needle according to claim 1,
  wherein the vertical cross-section at the maximal point closer to the needle tip has the cross-sectional area greater than that at another maximal point closer to the needle rear.

9. The medical needle according to claim 1,
  wherein the vertical cross-sections at the minimal points have the same cross-sectional area to each other.

10. The medical needle according to claim 1,
  wherein the vertical cross-section at the minimal point closer to the needle tip has the cross-sectional area less than that at another maximal point closer to the needle rear.

11. The medical needle according to claim 1,
  wherein the cross-sectional area of the vertical cross-section at the minimal point closest to the needle rear is less than those at any other minimal points.

12. The medical needle according to claim 1,
  wherein a distance between a pair of the adjacent maximal points is substantially equal to one between another pair of the adjacent maximal points.

13. The medical needle according to claim 1,
  wherein a pair of the adjacent maximal points closer to the needle tip is more spaced than another pair of the adjacent maximal points closer to the needle rear.

14. The medical needle according to claim 1, further comprising a grating.

15. The medical needle according to claim 1,
  wherein the needle tip has a radius of curvature of 10 µm or less.

16. The medical needle according to claim 1, further comprising a slit extending along the predetermined direction.

17. The medical needle according to claim 1,
  wherein the medical needle is made of biocompatible material.

18. The medical needle according to claim 1,
  wherein the medical needle is made of biodegradable material.

19. The medical needle according to claim 1,
  wherein when viewed on a projected plane parallel to the predetermined direction, the cross-sectional area varies in a curved manner between one of maximal points and the adjacent one of the minimal points.

20. A medical device including a medical needle extending along a predetermined direction and having a vertical cross-section taken along a plane perpendicular to the predetermined direction of which cross-sectional area varies based upon a distance from a needle tip, the medical needle, comprising:
  a plurality of maximal points where the cross-sectional area of the vertical cross-section is locally maximal; and
  a plurality of minimal points where the cross-sectional area of the vertical cross-section is locally minimal;
  wherein the vertical cross-section at the maximal point closest to the needle tip has the cross-sectional area not less than those at any other maximal points, and
  wherein the vertical cross-section between the needle tip and the maximal point closest to the needle tip is gradually and continuously increased in accordance with the distance from a needle tip.

* * * * *